(12) United States Patent
Oskin et al.

(10) Patent No.: US 12,016,533 B2
(45) Date of Patent: *Jun. 25, 2024

(54) STEERABLE MEDICAL DEVICE HAVING AN IMAGING SYSTEM

(71) Applicant: Boston Scientific Scimed, Inc., Maple Grove, MN (US)

(72) Inventors: Christopher L. Oskin, Grafton, MA (US); Brian C. MacLean, Westford, MA (US); William M. Asselin, Lunenburg, MA (US); Michael O'Brien, Newton, MA (US); Thomas M. Zappia, West Boylston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 867 days.

This patent is subject to a terminal disclaimer.

(21) Appl. No.: 17/074,714

(22) Filed: Oct. 20, 2020

(65) Prior Publication Data

US 2021/0030258 A1     Feb. 4, 2021

Related U.S. Application Data

(63) Continuation of application No. 16/282,794, filed on Feb. 22, 2019, now Pat. No. 10,842,361, which is a
(Continued)

(51) Int. Cl.
*A61B 1/00* (2006.01)
*A61B 1/005* (2006.01)
(Continued)

(52) U.S. Cl.
CPC ........ *A61B 1/0655* (2022.02); *A61B 1/00064* (2013.01); *A61B 1/00066* (2013.01);
(Continued)

(58) Field of Classification Search
CPC .......................... A61B 1/00066; A61B 1/0052
See application file for complete search history.

(56) References Cited

U.S. PATENT DOCUMENTS

| 4,580,551 A | 4/1986 | Siegmund et al. |
| 4,690,175 A * | 9/1987 | Ouchi ..................... B29C 63/18 138/131 |

(Continued)

FOREIGN PATENT DOCUMENTS

EP     2428157 A1     3/2012

OTHER PUBLICATIONS

International Search Report and Written Opinion for International Application No. PCT/US2013/020852, dated Jun. 14, 2013, 14 pages.

*Primary Examiner* — Timothy J Neal
(74) *Attorney, Agent, or Firm* — Bookoff McAndrews PLLC

(57) ABSTRACT

Embodiments of the disclosure may include a medical device comprising an elongate member and a handle assembly connected to the elongate member. The handle housing may house a steering mechanism movable relative to the handle assembly and configured to steer the elongate member along a first plane and a second plane different from the first plane, a camera system configured to capture images from a distal end of the elongate member, and an illumination system configured to provide illuminating light from the distal end of the elongate member.

14 Claims, 15 Drawing Sheets

Related U.S. Application Data continuation of application No. 14/792,425, filed on Jul. 6, 2015, now Pat. No. 10,251,534, which is a continuation of application No. 13/737,681, filed on Jan. 9, 2013, now abandoned.

(60) Provisional application No. 61/585,090, filed on Jan. 10, 2012.

(51) Int. Cl.
*A61B 1/015* (2006.01)
*A61B 1/018* (2006.01)
*A61B 1/05* (2006.01)
*A61B 1/06* (2006.01)
*A61B 1/307* (2006.01)

(52) U.S. Cl.
CPC ...... *A61B 1/00078* (2013.01); *A61B 1/00121* (2013.01); *A61B 1/00124* (2013.01); *A61B 1/005* (2013.01); *A61B 1/0051* (2013.01); *A61B 1/0052* (2013.01); *A61B 1/0057* (2013.01); *A61B 1/015* (2013.01); *A61B 1/018* (2013.01); *A61B 1/05* (2013.01); *A61B 1/0669* (2013.01); *A61B 1/0676* (2013.01); *A61B 1/307* (2013.01)

(56) References Cited

U.S. PATENT DOCUMENTS

| | | | |
|---|---|---|---|
| 4,753,222 A | 6/1988 | Morishita | |
| 4,899,787 A | 2/1990 | Ouchi et al. | |
| 5,299,560 A | 4/1994 | Hatori | |
| 5,634,881 A * | 6/1997 | Francis | A61B 1/002 600/920 |
| 5,810,715 A | 9/1998 | Moriyama | |
| 6,520,908 B1 * | 2/2003 | Ikeda | A61B 1/00066 600/110 |
| 6,749,560 B1 | 6/2004 | Konstorum et al. | |
| 7,922,650 B2 * | 4/2011 | McWeeney | A61B 1/00071 600/172 |
| 10,251,534 B2 * | 4/2019 | Oskin | A61B 1/0051 |
| 10,842,361 B2 * | 11/2020 | Oskin | A61B 1/0669 |
| 2002/0010386 A1 | 1/2002 | Matsushita et al. | |
| 2002/0026100 A1 | 2/2002 | Ouchi | |
| 2002/0151768 A1 | 10/2002 | Akiba | |
| 2003/0023142 A1 | 1/2003 | Grabover et al. | |
| 2004/0054254 A1 | 3/2004 | Miyake | |
| 2005/0065397 A1 | 3/2005 | Saadat et al. | |
| 2006/0171693 A1 | 8/2006 | Todd et al. | |
| 2006/0252992 A1 | 11/2006 | Mitsumori | |
| 2007/0232858 A1 | 10/2007 | Macnamara et al. | |
| 2008/0300462 A1 * | 12/2008 | Intoccia | A61B 1/0055 600/146 |
| 2009/0234280 A1 | 9/2009 | Tah et al. | |
| 2009/0247828 A1 * | 10/2009 | Watanabe | A61B 1/00066 600/131 |
| 2010/0076266 A1 | 3/2010 | Boulais et al. | |
| 2010/0121147 A1 | 5/2010 | Oskin et al. | |
| 2011/0009694 A1 | 1/2011 | Schultz et al. | |
| 2011/0112365 A1 | 5/2011 | Galperin et al. | |
| 2011/0112476 A1 | 5/2011 | Kauphusman et al. | |
| 2011/0295068 A1 * | 12/2011 | Petersen | A61B 1/05 600/131 |
| 2012/0065660 A1 | 3/2012 | Ferrera et al. | |

* cited by examiner

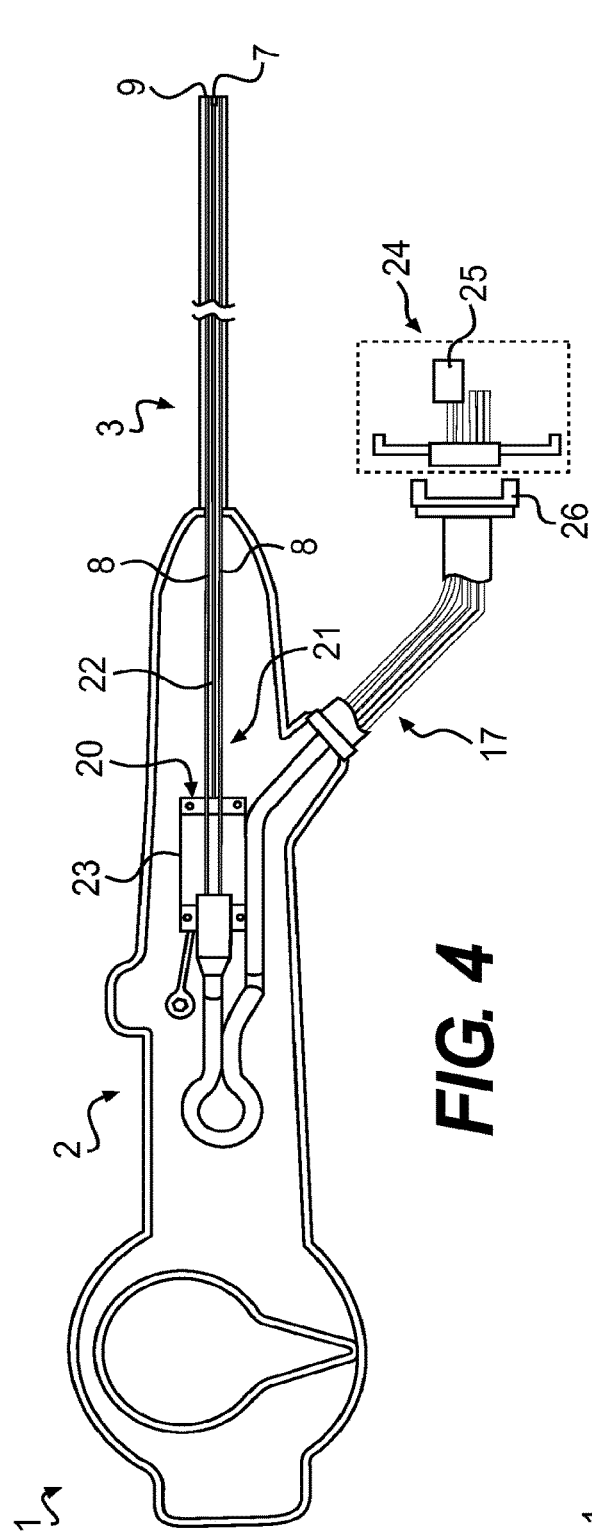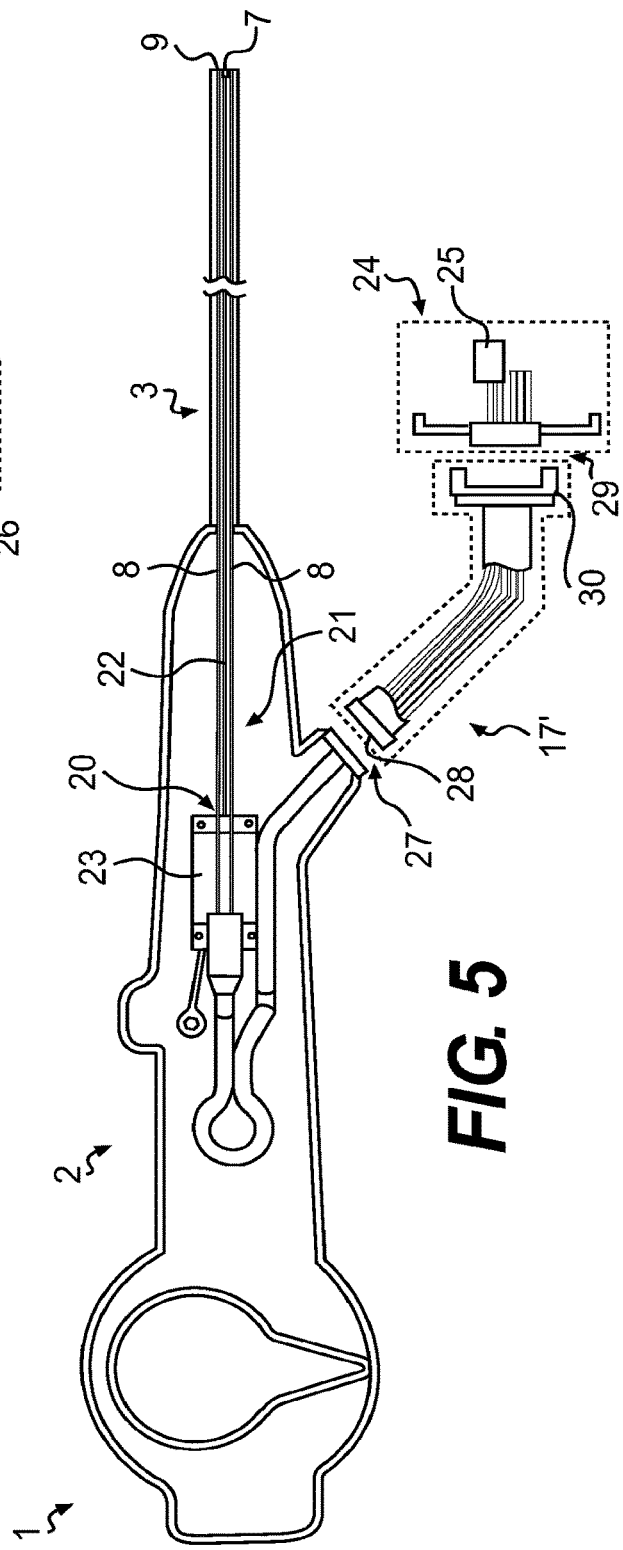

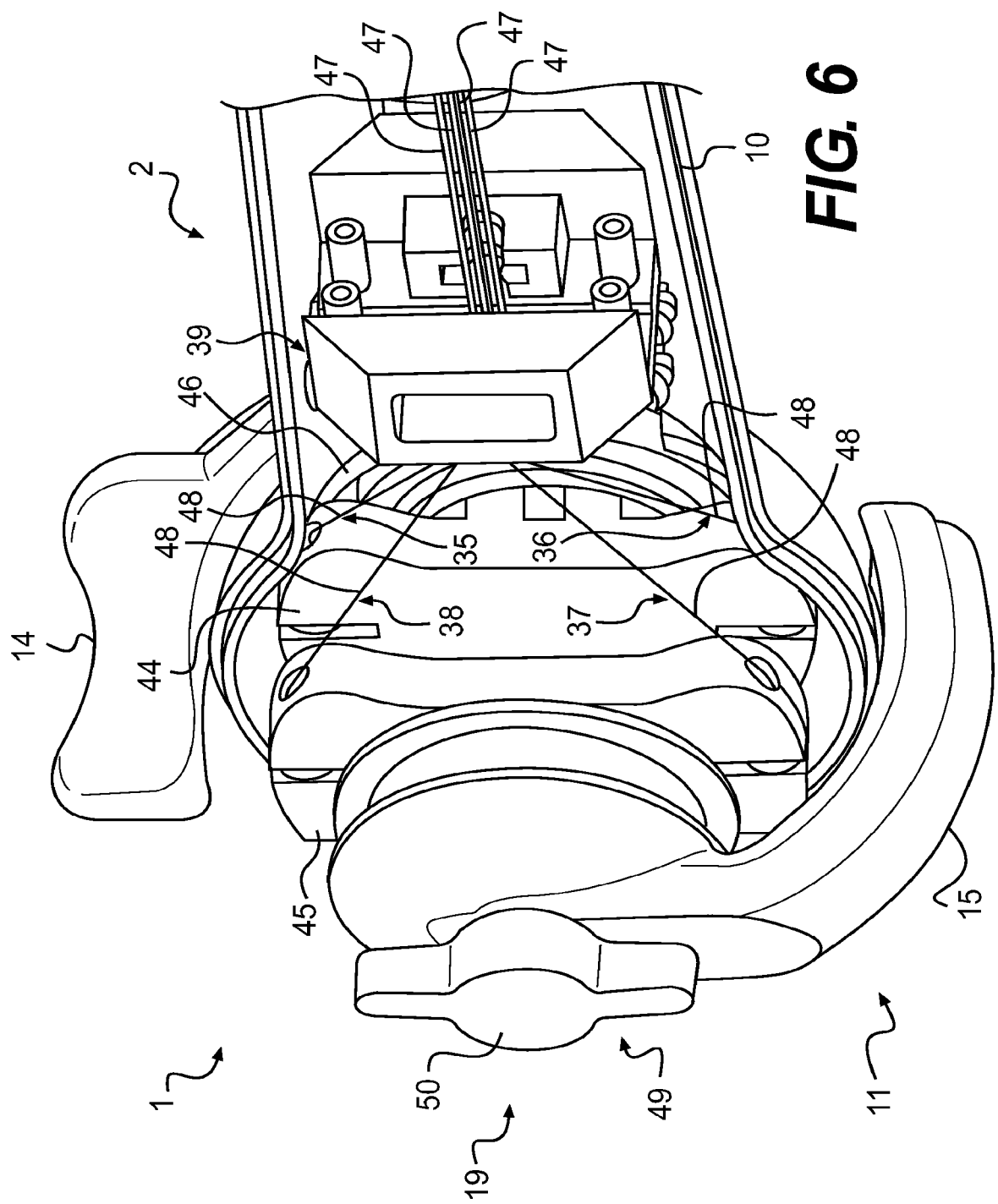

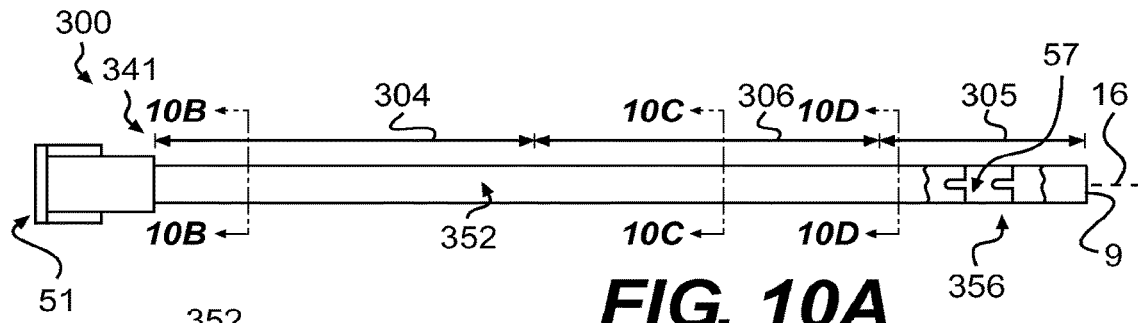
FIG. 10A
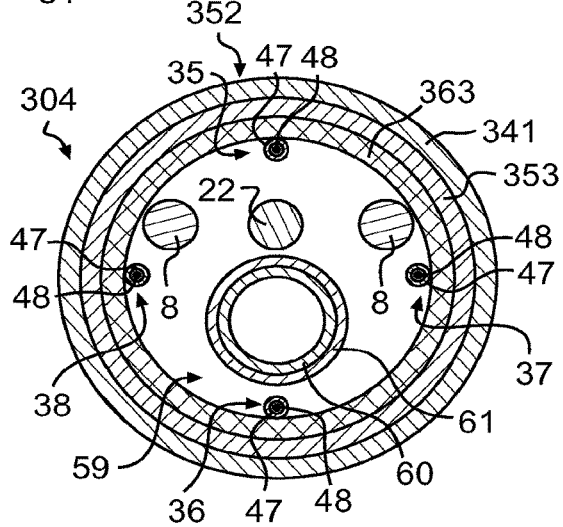
FIG. 10B
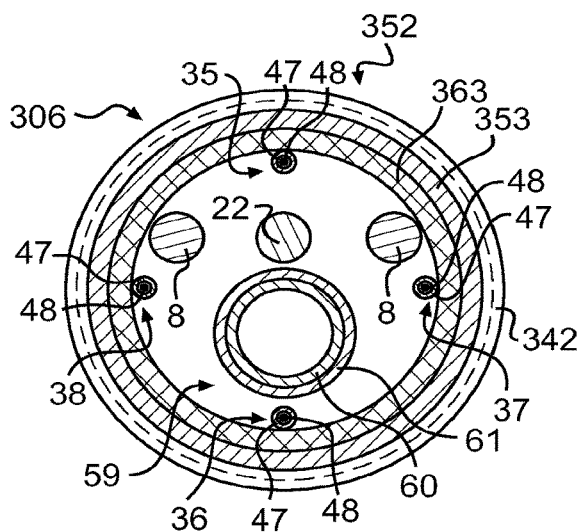
FIG. 10C
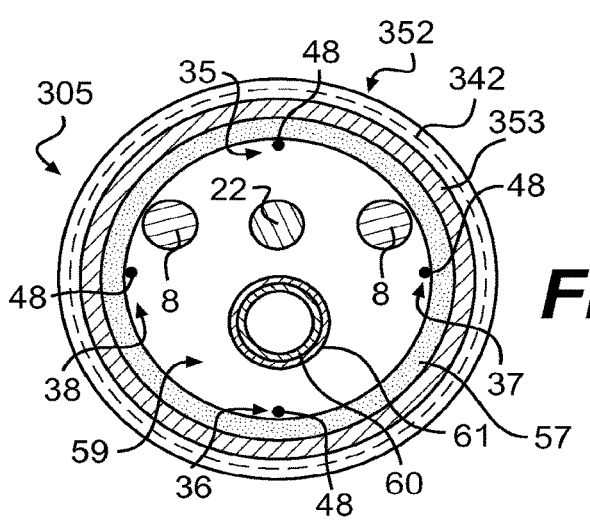
FIG. 10D

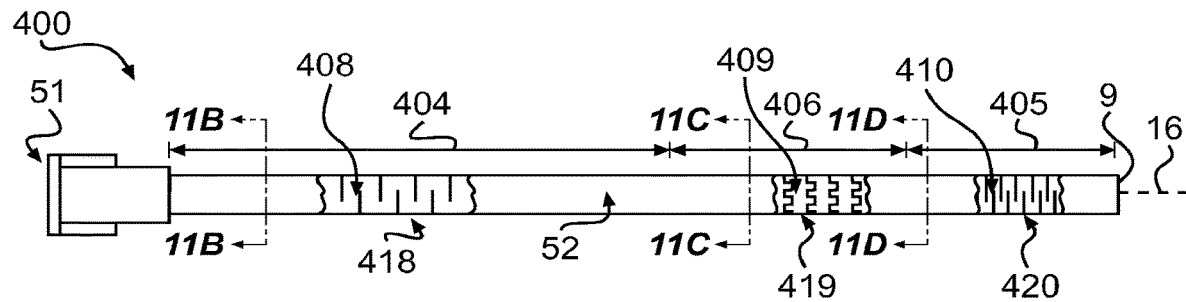
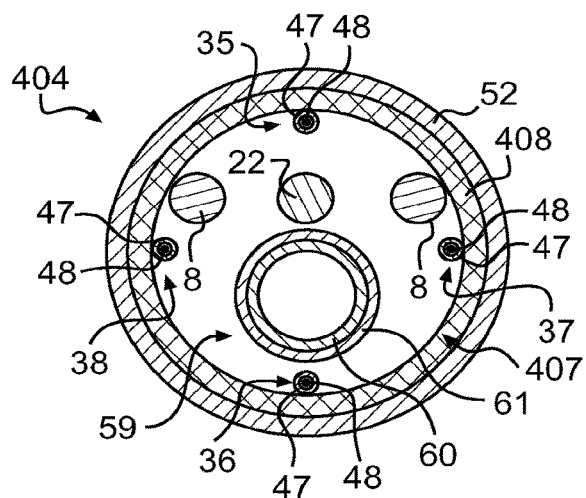
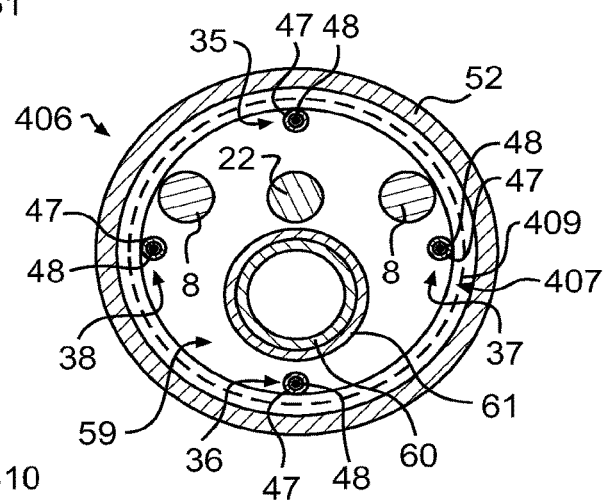
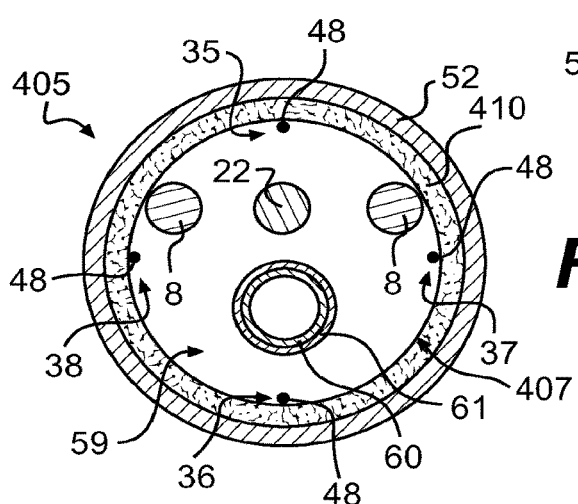

STEERABLE MEDICAL DEVICE HAVING AN IMAGING SYSTEM

CROSS-REFERENCE TO RELATED APPLICATIONS

This Application is a continuation of U.S. application Ser. No. 16/282,794, filed Feb. 22, 2019, which is a continuation of U.S. application Ser. No. 14/792,425, filed Jul. 6, 2015, now U.S. Pat. No. 10,251,534, which is a continuation of U.S. application Ser. No. 13/737,681, filed Jan. 9, 2013, now abandoned, which claims the benefit of priority of U.S. Provisional Application No. 61/585,090, filed Jan. 10, 2012, all of which are incorporated by reference herein in their entireties.

FIELD OF THE DISCLOSURE

Embodiments of the present disclosure include medical devices, and more particularly, ureteroscopes including a handle assembly housing an imaging system and a steering mechanism, and related methods of using such medical devices.

BACKGROUND

A challenge in the exploration and treatment of internal areas of the human anatomy has been adequately visualizing the area of concern. Visualization may be especially troublesome in minimally invasive procedures in which small diameter, elongate instruments, such as catheters or endoscopes, may be navigated through natural passageways and cavities of a patient to a treatment area.

Generally speaking, ureteroscopy is one procedure that may be performed to diagnosis and/or treat urinary tract diseases and ureteral strictures. In conventional ureteroscopy, a ureteroscope may be inserted retrograde through the urinary tract such that diagnosis and treatment of urinary tract abnormalities may occur under visualization. Ureteroscopes may include an elongate member that may encapsulate an image sensor, an illumination element, and a working channel. The working channel may allow for the passage of instruments, such as guidewires, stone retrieval baskets, and lasers. Moreover, some ureteroscopes may also incorporate a steering mechanism, which may be actuated by the user to deflect a distal tip of the elongate member in one or more planes. Steering may typically be achieved via ex-vivo manipulation at a handle end of the ureteroscope.

Problems exist, however, in the use of conventional ureteroscopes. For example, after each successive urological procedure, conventional ureteroscopes must be cleaned and sterilized before the next use, which delays successive procedures. Furthermore, conventional ureteroscopes are non-disposable and require extensive and expensive maintenance. Sterilization delays and costs associated with purchasing and/or repairing ureteroscopes have escalated costs for ureteroscopic procedures and other medical procedures that utilize similarly configured scopes. The medical devices and related methods of the present disclosure are directed to improvements in the existing technology.

SUMMARY

In accordance with an embodiment, a medical device may comprise an elongate member and a handle assembly connected to the elongate member. The handle housing may house a steering mechanism movable relative to the handle assembly and configured to steer the elongate member, a camera system configured to capture images from a distal end of the elongate member, and an illumination system configured to provide illuminating light from the distal end of the elongate member. The medical device may also comprise a connector configured to operably connect the medical device to a control module including one or more processing units for operating the camera system and the illumination system, wherein the connector may be configured to directly connect to and disconnect from the handle assembly.

Various embodiments of the disclosure may include one or more of the following aspects: the steering mechanism may be configured to steer the elongate member along a first plane and a second plane different from the first plane; the connector may extend into the handle assembly and may be configured to connect and disconnect the camera system and the illumination system to the control module; the camera system may include a camera card housed within the housing assembly and may be configured to communicate imaging data associated with the camera system; the camera system may include one or more wires housed within the housing assembly, wherein the one or more wires may extend through the elongate member and may operably connect to an image sensor at a tip of the elongate member; the camera card and the one or more wires may be configured to operably connect to the connector; the illumination system may include one or more illumination units within the housing assembly and may extend through the elongate member, wherein the one or more illumination units may be configured to operably connect to the connector; a tool port may be configured to deliver a tool through the elongate member, and a fluid port may be configured to deliver fluid through the elongate member, wherein the tool port and the fluid port may form a Y-shaped structure extending from the handle assembly; the connector may extend from the handle assembly via a connector hub, wherein the connector hub may be positioned on a distal end of the handle assembly and may be angled towards the elongate member; the steering mechanism may include a first cam, a second cam, and a plurality of control members housed within the housing assembly, wherein the plurality of control members may be operably coupled to the first and second cams and may extend through the elongate member, and wherein the plurality of control members may be coupled to a distal portion of the elongate member; and the steering mechanism may include a first actuator operably coupled to the first cam and a second actuator operably coupled to the second cam, wherein actuation of the first actuator may steer the distal portion of the elongate member along the first plane, and actuation of the second actuator may steer the distal portion of the elongate member along the second plane.

In accordance with another embodiment, an elongate member for a medical device may comprise a proximal portion including a proximal combination of layers of material configured to provide pushability of the elongate member, a medial portion including a medial combination of layers of material configured to provide passive deflection of the elongate member, and a distal portion including a distal combination of layers of material configured to provide active deflection of the elongate member, wherein the proximal combination, the medial combination, and the distal combination may be different from each other.

Various embodiments of the disclosure may include one or more of the following aspects: the elongate member may house one or more control members, one or more illumination units, an image sensor, and a working channel; the proximal combination may include an inner layer of a coiled material and an outer layer of a polymeric material, the medial combination may include an inner layer of a coiled material having a laser cut pattern and an outer layer of the polymeric material, and the distal combination may include an inner layer of a plurality of articulation joints and an outer layer of the polymeric material; the proximal combination may include an innermost layer of a coiled material, a middle layer of a braided material, and an outer layer of a first polymeric material; the medial combination may include an innermost layer of the coiled material, a middle layer of the braided material, and an outer layer of a second polymeric material less rigid than the first polymeric material; and the distal combination may include an innermost layer of a plurality of articulation joints, a middle layer of the braided material, and an outer layer of the second polymeric material; the proximal combination may include an inner layer formed of a tube having a first laser cut pattern and an outer layer of a polymeric material, the medial combination may include an inner layer formed of a tube having a second laser cut pattern different than the first laser cut pattern and an outer layer of the polymeric material, and the distal combination may include an inner layer formed of a tube having a third laser cut pattern different than the first laser cut pattern and the second laser cut pattern and an outer layer of the polymeric material; the distal combination may include a first layer of a polymeric material molded over the one or more control members, a second layer surrounding the first layer and formed of a coiled material, a third layer surrounding the first and second layers and formed of a first polymeric material, and a fourth layer surrounding the first, second, and third layers and formed of a second polymeric material different than the first polymeric material; the elongate member may include a tip having an opening for one or more illumination units, an opening for an image sensor, and an opening for a working channel; the opening for the one or more illumination units may include a diffuser; and the opening for the one or more illumination units may curve at least partially around the opening for the image sensor.

In this respect, before explaining multiple embodiments of the present disclosure in detail, it is to be understood that the present disclosure is not limited in its application to the details of construction and to the arrangements of the components set forth in the following description or illustrated in the drawings. The present disclosure is capable of embodiments in addition to those described and of being practiced and carried out in various ways. Also, it is to be understood that the phraseology and terminology employed herein, as well as the abstract, are for the purpose of description and should not be regarded as limiting.

The accompanying drawings illustrate certain exemplary embodiments of the present disclosure, and together with the description, serve to explain the principles of the present disclosure. As such, those skilled in the art will appreciate that the conception upon which this disclosure is based may readily be used as a basis for designing other structures, methods, and systems for carrying out the several purposes of the present disclosure. It is important, therefore, to recognize that the claims should be regarded as including such equivalent constructions insofar as they do not depart from the spirit and scope of the present disclosure.

BRIEF DESCRIPTION OF THE DRAWINGS

FIG. 4 illustrates a schematic view of the medical device of FIG. 1 operably connected to a control module, according to an exemplary disclosed embodiment;

FIG. 5 illustrates a schematic view of the medical device of FIG. 1 operably connected to a control module, according to an exemplary disclosed embodiment;

FIG. 6 illustrates a perspective view of inner parts of the handle assembly of the medical device of FIG. 1, according to an exemplary disclosed embodiment;

FIG. 10A illustrates a schematic view of another elongate member of a medical device, according to an exemplary disclosed embodiment;

FIG. 10B illustrates a cross-sectional view of the elongate member of FIG. 10A, according to an exemplary disclosed embodiment;

FIG. 10C illustrates another cross-sectional view of the elongate member of FIG. 10A, according to an exemplary disclosed embodiment;

FIG. 10D illustrates another cross-sectional view of the elongate member of FIG. 10A, according to an exemplary disclosed embodiment;

FIG. 11A illustrates a schematic view of another elongate member of a medical device, according to an exemplary disclosed embodiment;

FIG. 11B illustrates a cross-sectional view of the elongate member of FIG. 11A, according to an exemplary disclosed embodiment;

FIG. 11C illustrates another cross-sectional view of the elongate member of FIG. 11A, according to an exemplary disclosed embodiment;

FIG. 11D illustrates another cross-sectional view of the elongate member of FIG. 11A, according to an exemplary disclosed embodiment;

DETAILED DESCRIPTION

Reference will now be made in detail to the exemplary embodiments of the present disclosure described above and illustrated in the accompanying drawings.

The terms "proximal" and "distal" are used herein to refer to the relative positions of the components of an exemplary medical device. When used herein, "proximal" refers to a position relatively closer to the exterior of the body or closer to the physician, or other user, using the medical device. In contrast, "distal" refers to a position relatively further away from the surgeon, or other user, using the medical device or closer to the interior of the body.

Figure 1:
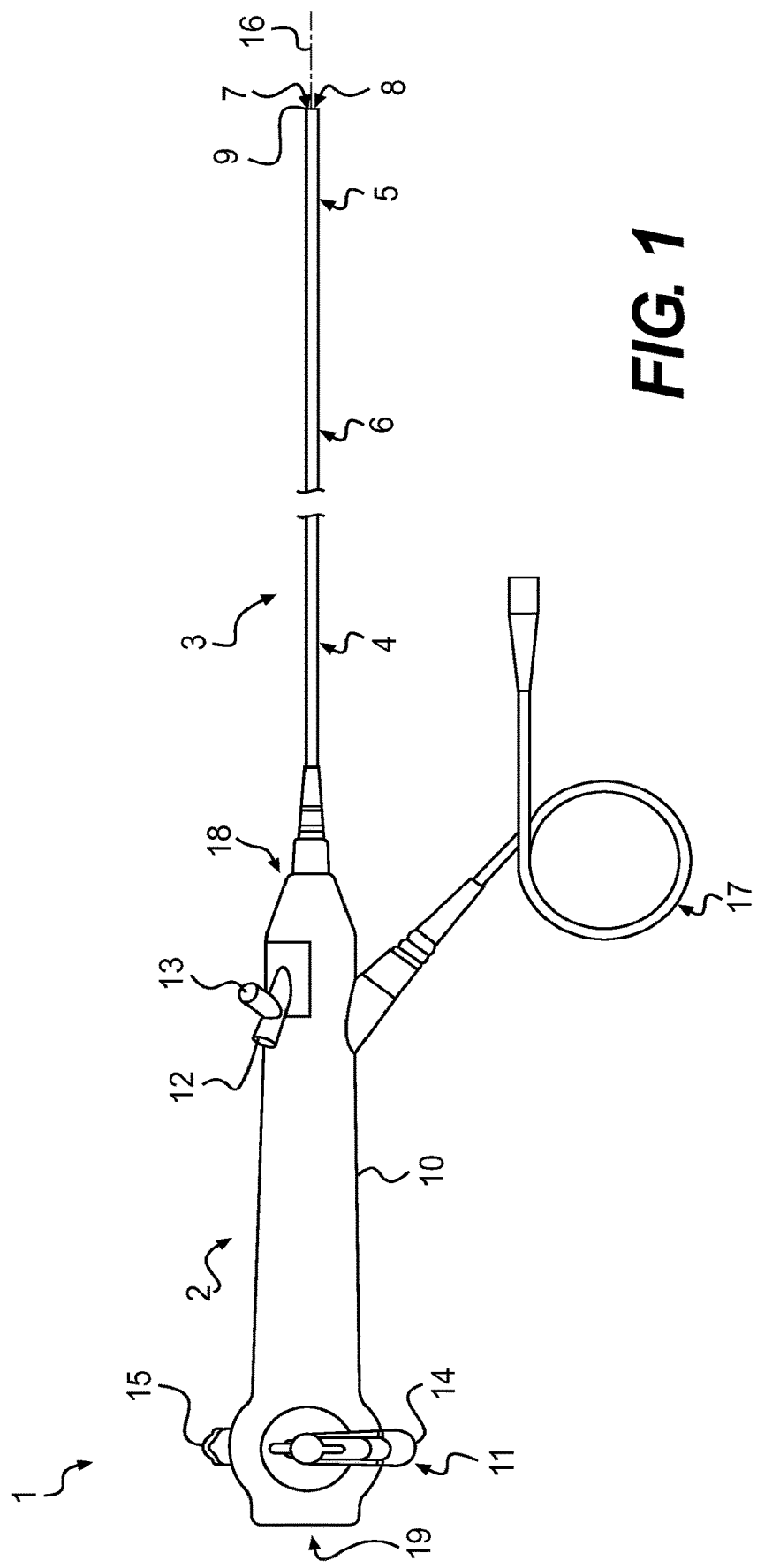
FIG. 1 illustrates a medical device, according to an exemplary disclosed embodiment.

FIG. 1 illustrates a medical device 1 according to an exemplary embodiment. Medical device 1 may be any device configured to allow an operator to access and view internal body anatomies of a patient, as well as to deliver medical instruments, such as, for example, biopsy forceps, graspers, baskets, snares, probes, scissors, retrieval devices, lasers, and other tools, into the patient's body. Medical device 1 may be inserted into a variety of body lumens and/or cavities, such as, for example, any portion of a urinary tract including a ureter, a gastrointestinal lumen including an esophagus, a vascular lumen, an airway, and the like.

For the purposes of the present disclosure, medical device 1 may be a sterile, single-use, and disposable ureteroscope. Other types of devices, however, may be substituted for the ureteroscope, including, as examples, an endoscope, a hysteroscope, a uteroscope, a bronchoscope, a cystoscope, and the like.

Ureteroscope 1 may include a handle assembly 2 and an elongate member 3 operably connected to handle assembly 2. Elongate member 3 may be, for example, a catheter, and configured to be at least partially inserted into a body of a patient. Elongate member 3 may be flexible, or may include one or more portions that are flexible, to allow elongate member 3 to be maneuvered within the body and traverse tortuous anatomical lumens. For instance, elongate member 3 may be uniformly flexible or may include a plurality of portions having varying degrees of flexibility or rigidity. Elongate member 3 may include a proximal portion 4, a distal portion 5, and a medial portion 6 disposed between proximal portion 4 and distal end portion 5.

An image sensor 7 and an illumination unit 8 may be located at a tip 9 of elongate member 3. Image sensor 7 may be configured to capture images and/or full-motion video images. Illumination unit 8 may be configured to illuminate internal body pathways and/or cavities of a patient.

Handle assembly 2 may include a handle housing 10 to which one or more ports 12, 13 and a steering mechanism 11 may be operably coupled.

Ports 12, 13 may provide access to one or more channels extending through elongate member 3. For example, port 12 may provide access for one or more medical tools to a working channel extending through elongate member 3 and out tip 9. Additionally, port 13 may provide access through the working channel for a suitable fluid, such as water or gas, for, as examples, irrigation and insufflation purposes.

Steering mechanism 11 may be configured to control the steering and deflection of distal portion 5 of elongate member 3. Steering mechanism 11 may include a first actuator 14 and a second actuator 15 configured to control deflection of distal portion 5 between a substantially linear configuration and a curved, angled, or bent configuration. Distal portion 5 may be moved to a variety of different curved, angled, or bent configurations in a variety of different directions relative to a longitudinal axis 16 of elongate member 3. For example, actuating first actuator 14 up and down relative to longitudinal axis 16 of elongate member 3 may cause distal portion 5 to deflect in a first direction and a second direction of a first plane, and actuating second actuator 15 side-to-side relative to longitudinal axis 16 of elongate member 3 may cause distal portion 5 to deflect in a first direction and a second direction of a second plane different than the first plane. Accordingly, steering mechanism 11 may provide four-way steering of distal portion 5 of elongate member 3; however, it should also be appreciated that steering mechanism 11 may provide less or greater than four-way steering of distal portion 5, depending on, for example, the volume and/or the shape of the internal body anatomies which may be traversed by elongate member 3.

A connector 17 may also be coupled to handle assembly 2. As will be described in more detail below, connector 17 may be configured to operably connect and disconnect ureteroscope 1 to a suitable control module. Although connector 17 is illustrated in FIG. 1 as projecting at an angle near a distal end 18 of handle assembly 2, it should also be appreciated that in certain embodiments, connector 17 may extend from a proximal end 19 of handle assembly 2.

Figure 2:
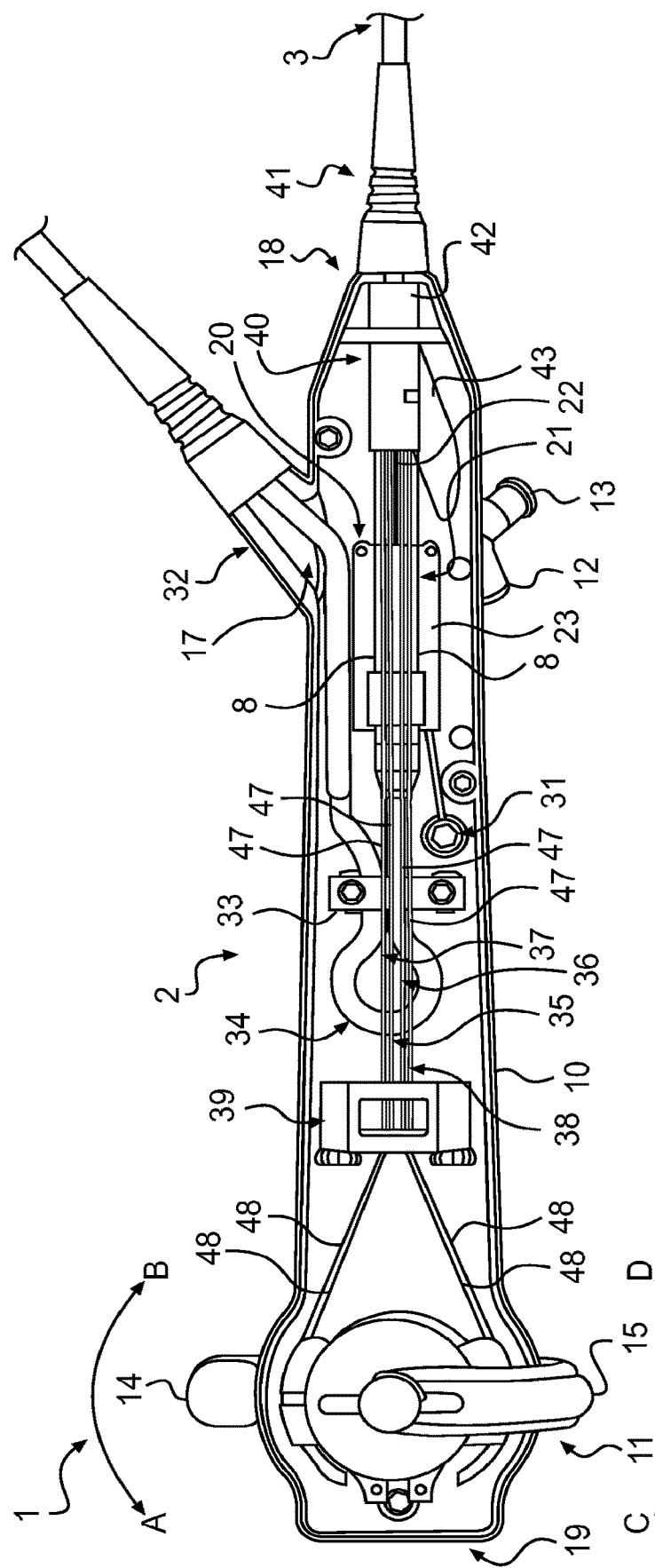
FIG. 2 illustrates a plan view of parts of a handle assembly of the medical device of FIG. 1, according to an exemplary disclosed embodiment.

FIG. 2 illustrates a plan view of inner parts of handle assembly 2 of ureteroscope 1 according to an exemplary embodiment. Handle assembly 2 may include handle housing 10 comprising two half-portions (only one half-portion shown in FIG. 2) joined together by appropriate removable fasteners, such as screws and pins, or by appropriate non-removable fastening techniques, such as heat bonding. Handle housing 10 may house a camera system 20, an illumination system 21, steering mechanism 11, and connector 17.

Figure 3:
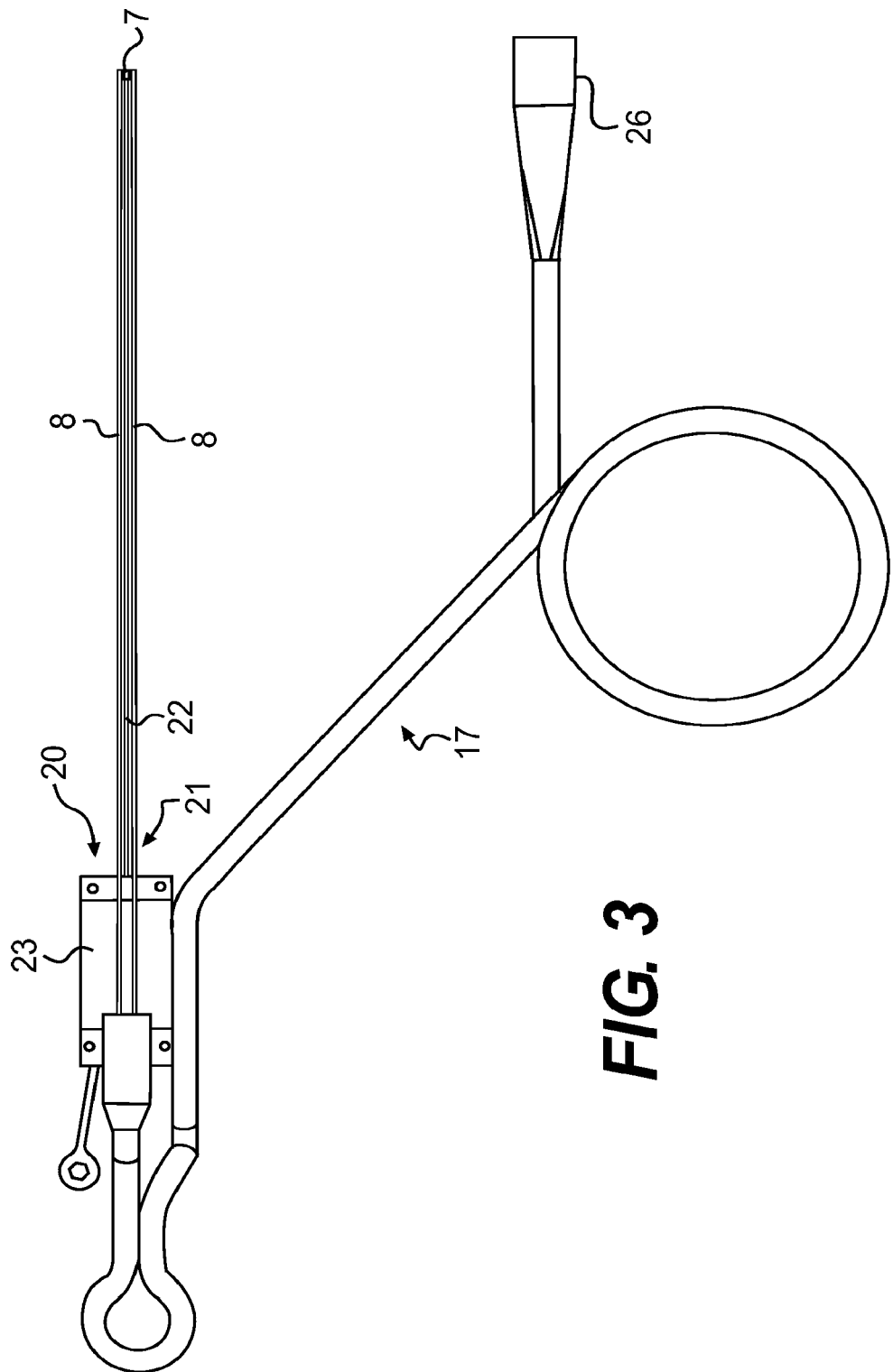
FIG. 3 illustrates a camera system, an illumination system, and a connector of the medical device of FIG. 1, according to an exemplary disclosed embodiment.

FIG. 3 illustrates camera system 20, illumination system 21, and connector 17 separated from handle housing 10 according to an exemplary embodiment. Camera system 20 and illumination system 21 may form a single, operating unit. In other words, a single connector 17 may communicate image and illumination data between the suitable control module and camera system 20 and illumination system 21.

Camera system 20 may include image sensor 7, one or more electrical wires 22, and camera card 23. As discussed above, image sensor 7 may be any suitable type of image sensor configured to capture images and/or full-motion video images in digital or any other suitable format, such as, for example, a camera including a charged couple device (CCD) or a CMOS image sensor. Image sensor 7 may include a pixel count greater than 20,000 pixels and less than 70,000 pixels. In addition, image sensor 7 may include a field of view of at least 80°. One or more electrical wires 22 may be operably coupled to image sensor 7 and connector 17. Thus, image data captured by image sensor 7 may be transmitted through one or more electrical wires 22, through connector 17, and to the control module. Camera card 23 may also be connected to image sensor 7 via one or more electrical wires 22 and to connector 17. Camera card 23 may be, for example, any suitable circuit board configured to calibrate the captured images based on commands from the control module. For example, camera card 23 may include appropriate circuitry and memory and may deserialize image data from image sensor 7 and may perform known algorithms, such as demosaicing, gain control, and white balance, to produce a quality color image. The gain control may be implemented by adjusting the intensity of illumination system 21 and adjusting the gains applied to the signals by image sensor 7. Camera card 23 may also include isolation circuitry to prevent unacceptable radio frequency susceptibility, emissions and interference, as well as unacceptable leakage currents in the event of an electrical failure. Camera card 23 may also include circuitry for transmitting control signals to image sensor 7 from the control module and for receiving image data from the image sensor 7 and delivering the image data to the control module. Moreover, camera system 20 may include one or more features of the imaging system disclosed in U.S. Patent Application Publication No. 2010/0076266 to Boulais et al., which is incorporated herein by reference in its entirety.

Illumination system 21 may include illumination unit 8 operably connected to connector 17. For the purposes of the present disclosure, illumination unit 8 may include, for example, one or more fiber optic cables configured to deliver light to a distal tip of fiber optic cables located at tip 9 of elongate member 3. It should be appreciated, however, that the fiber optic cables may be substituted for any known illumination device, such as, for example, illumination light emitting diodes (LEDs), illumination lenses, illumination rods, illumination mirrors, solid light guides (e.g., lasers), and incandescent bulbs.

FIG. 4 illustrates a schematic representation of ureteroscope 1 coupled to a control module 24 according to an exemplary embodiment. As alluded to above, control module 24 may include imaging electronics configured to process and/or transfer signals received from camera system 20, signals controlling camera system 20, and patient image data to a display (not shown) for viewing by a user. Control module 24 may also include an appropriate illumination source 25, such as a halogen source or an LED source, configured to deliver light to illumination unit 8, and illumination electronics configured to process and/or transfer signals controlling illumination source 25. One or more actuators or buttons may be disposed on control module 24 to control illumination source 25 and camera system 20. Alternatively, the one or more actuators or buttons may be disposed on handle assembly 2. Furthermore, control module 24 may include one or more features of the control cabinet disclosed in U.S. Patent Application Publication No. 2010/0076266 to Boulais et al.

As illustrated in FIGS. 3 and 4, connector 17 may operably connect handle assembly 2 to control module 24 and provide a communication pathway between control module 24 and both camera system 20 and illumination system 21. For example, connector 17 may provide electronic signaling pathways for image sensor 7 to transmit image data to control module 24, for control module 24 to transmit image control signals to image sensor 7 and camera card 23, and for control module 24 to control light delivered from illumination source 25 to illumination unit 8. In some embodiments, connector 17 may operably connect illumination unit 8 to illumination source 25 contained in control module 24. It should be appreciated that in other embodiments, however, illumination source 25 may be housed in handle assembly 2, and illumination unit 8 may be operably connected to illumination source 25 within handle assembly 2. Illumination source 25 may then be operably coupled to control module 24 via connector 17.

Connector 17 may include any appropriate linkage configured to provide signaling capabilities and communication between control module 24 and both camera system 20 and illumination system 21, such as, for example, one or more electrical wires, an electrical conduit, and the like. Connector 17 may also include a suitable structure 26 configured to readily attach to control module 24 and detach from control module 24, such as, for example, a detachable point-to-point adapter, a detachable splice, and a detachable multi-port adapter. Accordingly, connector 17 may operably link ureteroscope 1 to control module 24 when, for example, performing a procedure utilizing camera system 20 and illumination system 21, and may readily detach ureteroscope 1 from control module 24 when, for example, the procedure is completed, and the ureteroscope 1 is to be disposed.

As shown in FIG. 4, connector 17 may be fixed to handle assembly 2, and thus, the entire ureteroscope 1 may be attached and detached from control module 24 by connecting and disconnecting connector 17 from control module 24.

FIG. 5 illustrates another schematic representation of ureteroscope 1 coupled to control module 24 according to an exemplary embodiment. As shown in FIG. 5, a connector 17' may be separately detachable from both handle assembly 2 and control module 24. In other words, a handle end 27 of connector 17' may include a first structure 28 configured to readily attach to and detach from handle assembly 2. First structure 28 may provide a communication linkage between connector 17' and illumination system 21 and camera system 20. A control module end 29 of connector 17' may include a second structure 30 also configured to readily attach to and detach from control module 24. Second structure 30 may provide a communication linkage between connector 17' (and thus ureteroscope 1) and control module 24. Such a configuration may provide a reusable connector 17' for subsequent procedures. In other words, once a procedure is completed, ureteroscope 1 may be disposed, and connector 17' may be sterilized and reused with a new ureteroscope 1 for another procedure. Alternatively, connector 17', like ureteroscope 1, may be readily detached from control module 24 and disposed. In certain embodiments, it should be appreciated that connector 17' may be fixedly attached to control module 24 and readily detachable from handle assembly 2. Accordingly, ureteroscope 1 may be readily detached from connector 17' and control module 24 and disposed after a procedure, and connector 17' may be reused with a new ureteroscope 1 for a subsequent procedure.

Referring back to FIG. 2, camera system 20 and illumination system 21 may be secured within handle housing 10 by any suitable means. For example, camera card 23 may be fastened to handle housing 10 by appropriate fasteners, such as screws and pins, or by appropriate fastening techniques, such as heat bonding and adhesive bonding. Furthermore, camera card 23 may be attached to a suitable grounding means 31 to discharge errant electrical surges and prevent damage to camera board 23 from said surges. It should also be appreciated that camera board 23 may be hermetically-sealed in a fluid tight encapsulation to prevent damage from liquids.

One or more electrical wires 22 may extend from handle housing 10, through elongate member 3, and connect to image sensor 7 located at tip 9 of elongate member 3. Illumination unit 8 may also extend from handle housing 10, through elongate member 3, and terminate at tip 9 of elongate member 3.

Connector 17 may extend from inside of handle housing 10 and exit handle housing 10 via a connector hub 32. Connector 17 may be secured to handle housing 10 by a suitable anchoring device 33, such as a strap, brace, and the like. Connector 17 may include a looped portion 34 positioned within handle housing 10. Looped portion 34 may prevent undesired kinking of the communication linkage (e.g., electrical wires) associated with connector 17.

Steering mechanism 11 may be housed within handle housing 10 at proximal end 19 of handle assembly 2. As shown in FIG. 2, in addition to first actuator 14 and second actuator 15, steering mechanism 11 may include a first control member 35, a second control member 36, a third control member 37, a fourth control member 38, and a control member holding mechanism 39. Control members 35, 36, 37, 38 may be coupled to first and second actuators 14, 15 and extend along handle housing 10 and through elongate member 3. Furthermore, control members 35, 36, 37, 38 may each be coupled to elongate member 3 at or near tip 9.

A shaft hub 40 may be positioned within handle housing 10 near distal end 18 of handle assembly 2. Shaft hub 40 may be a Y-shaped structure and may be insert molded to connect a proximal end 41 of elongate member 3 to handle assembly 2. Shaft hub 40 may include a first conduit 42 and a second conduit 43. First conduit 42 may lead control members 35, 36, 37, 38, one or more electrical wires 22 of camera system 20, and illumination unit 8 of illumination system 21 into a lumen defined by elongate member 3. Second conduit 43 may lead a tube fluidly coupled to ports 12, 13 into the working channel extending through elongate member 3. Accordingly, one or more tools may be delivered through port 12 and through the working channel of elongate member 3, and irrigation fluid or insufflation gas may be delivered through the working channel of elongate member 3 via port 13, without interfering with and potentially damaging control members 35, 36, 37, 38, one or more electrical wires 22, and illumination unit 8.

FIG. 6 illustrates a perspective view of parts of handle assembly 2 of ureteroscope 1 according to an exemplary embodiment. As shown in FIG. 6, steering mechanism 11 may also include a first cam 44 coupled to first actuator 14 and a second cam 45 coupled to second actuator 15. First cam 44 and second cam 45 may be disposed within handle housing 10 and supported in handle housing 10 by a frame 46. First cam 44 and second cam 45 may be rotatably supported by a central arm, such as a boss (not shown), and each of first cam 44 and second cam 45 may be separately rotatable in response to actuation of first actuator 14 and second actuator 15, respectively.

First cam 44 may be coupled to first control member 35 and second control member 36. As illustrated in FIG. 6, first and second control members 35, 36 may be coupled to first cam 44 at spaced locations. First control member 35 may be coupled to a portion of first cam 44 proximate to first actuator 14 (such as an end of cam 44 closest to actuator 14). Second control member 36 may be coupled to a portion of first cam 44 different than the portion of first cam 44 coupled to first control member 35 (such as an end of cam 44 furthest from actuator 14). Moreover, first control member 35 and second control member 36 may be positioned in respective slots on first cam 44 and secured thereto by any suitable fastener, such as screws, pins, and adhesives. First control member 35 and second control member 36 each may be adapted to move in response to movement of first cam 44. As discussed, first control member 35 and second control member 36 may be coupled to elongate member 3 at or near tip 9. Thus, first control member 35 and second control member 36 may deflect and steer elongate member 3 by actuation of first actuator 14.

First actuator 14 may be moved towards proximal end 19 and towards distal end 18 of handle assembly 2. In other words, first actuator 14 may be rotated towards direction "A" and rotated towards direction "B", as indicated by the directional arrow shown in FIG. 2. As first actuator 14 is moved, first cam 44 may correspondingly rotate relative to frame 46 and handle housing 10.

For instance, when first actuator 14 is moved towards proximal end 19 of handle assembly 2 (i.e., towards direction A shown in FIG. 2), first cam 44 may rotate and move (or pull on) first control member 35. First control member 35 then may move distal portion 5 of elongate member 3 in the first direction along the first plane (e.g., up). First actuator 14 may be moved towards distal end 18 of handle assembly 2 (i.e., towards direction B shown in FIG. 2) to return elongate member 3 to its starting position (or a linear or relaxed position). In some embodiments, at least one of first actuator 14 and first cam 44 may be biased such that elongate member 3 may be maintained at the linear or relaxed position. When first actuator 14 is moved further towards distal end 18, first cam 44 may rotate and move (or pull on) second control member 36. Second control member 36 then may move distal portion 5 of elongate member 3 in the second direction along the first plane (e.g., down).

Similar to first cam 44, second cam 45 may be coupled to third control member 37 and fourth control member 38. As illustrated in FIG. 6, third and fourth control members 37, 38 may be coupled to second cam 45 at spaced locations. Third control member 37 may be coupled to a portion of second cam 45 proximate to second actuator 15 (such as an end of cam 45 closest to actuator 15). Fourth control member 38 may be coupled to a portion of second cam 45 different than the portion of second cam 45 coupled to third control member 37 (such as an end of cam 45 furthest from actuator 15). Moreover, third control member 37 and fourth control member 38 may be positioned in respective slots on second cam 45 and secured thereto by any suitable fastener, such as screws, pins, and adhesives. Third control member 37 and fourth control member 38 each may be adapted to move in response to movement of second cam 45. As discussed, third control member 37 and fourth control member 38 may also be coupled to elongate member 3 at or near tip 9. Thus, third control member 37 and fourth control member 38 may deflect and steer elongate member 3 by actuation of second actuator 15.

Second actuator 15 may also be moved towards proximal end 19 and towards distal end 18 of handle assembly 2. In other words, second actuator 15 may be rotated towards direction "C" and rotated towards direction "D", as indicated by the directional arrow shown in FIG. 2. As second actuator 15 is moved, second cam 45 may correspondingly rotate relative to frame 46 and handle housing 10.

For instance, when second actuator 15 is moved towards proximal end 19 of handle assembly 2 (i.e., towards direction C shown in FIG. 2), second cam 45 may rotate and move (or pull on) third control member 37. Third control member 37 then may move distal portion 5 of elongate member 3 in the first direction along the second plane (e.g., left). Second actuator 15 may be moved towards distal end 18 of handle assembly 2 (i.e., towards direction D shown in FIG. 2) to return elongate member 3 to the linear or relaxed position. Similar to first actuator 14 and first cam 44, in some embodiments, at least one of second actuator 15 and second cam 45 may be biased such that elongate member 3 is maintained at the linear or relaxed position. When second actuator 15 is moved further towards distal end 18, second cam 45 may rotate and move (or pull on) fourth control member 38. Fourth control member 38 then may move distal portion 5 of elongate member 3 in the second direction along the second plane (e.g., right).

As shown in FIGS. 2 and 6, control members 35, 36, 37, 38 may each be a Bowden cable including an outer jacket 47 and an inner control wire 48. Bowden cables may be configured to transmit a mechanical pulling force by movement of inner control wires 48 relative to outer jackets 47. More particularly, outer jackets 47 may be configured to help transfer the point of relative motion from distal end portions of control wires 48 to more proximal portions of wires 48.

Outer jacket 47 may be constructed of any suitable material. For example, outer jacket 47 may be of a composite construction, such as a spiral steel wire coated with plastic, or may be a single material, such as a plastic or polymeric sheath. Control wire 48 may also be constructed of any suitable material, such as stainless steel, tungsten, and Nitinol. Moreover, wire 48 may be a braided or bundled configuration of a plurality of materials, including, for example, a polymeric tube filled with graphite, or may be a single strand of material, such as a stainless steel wire or conduit.

Control members 35, 36, 37, 38 may each be anchored within handle housing 10 by control member holding mechanism 39. Control member holding mechanism 39 may also be configured to relieve tension to control members 35, 36, 37, 38. Particularly, control member holding mechanism 39 may include a sliding block not shown) and a spring arrangement (not shown) coupled to each of control members 35, 36, 37, 38, similar to the steering system tension control device disclosed in U.S. Patent Application Publication No. 2007/0232858 to Macnamara et al., which is incorporated herein by reference in its entirety. Particularly, outer jackets 47 of control members 35, 36, 37, 38 may be fixed to the slidable block, and control wires 48 may extend proximally from the slidable block and may be coupled to the first and second actuators 14, 15. The spring may be positioned between the slidable block and a proximal abutment (not shown) of control member holding mechanism 39. When outer jackets 47 are under compression (due to, e.g., significant bending or steering of the elongate member 3) sufficient to overcome the counteracting force of the spring, the slidable block will give and proximally slide to compress the spring. Such action may relieve the compression on one or all of outer jackets 37, thereby relieving the tension on control wires 48 and making control wires 48 easier to move. It should be appreciated that the tension in control wires 48 may not be allowed to exceed a predetermined limit that may be set to be the spring force of the spring.

Steering mechanism 11 may also include a lock system 49 configured to lock elongate member 3 in a desired linear or deflected position in response to an actuation by second actuator 15. Lock system 49 may be similar to the lock mechanism disclosed in U.S. Pat. No. 7,922,650 to McWeeney et al., which is incorporated herein by reference in its entirety. Lock system 49 may include a tension knob 50 configured to actuate between a locked position, selectively tensioned positions, and an unlocked position. In use, a user may adjust the tension of second actuator 15, as desired, by rotation of tension knob 50. Further tightening of tension knob 50 may prevent actuation of second actuator 15, thereby locking third and fourth control members 37, 38, and in turn, locking the linear or deflected position of elongate member 3. Although not illustrated in FIG. 6, it should also be appreciated that a similar lock system may be associated with first actuator 14 that may be configured to lock elongate member 3 in a desired linear or deflected position in response to an actuation by first actuator 14.

Figure 7:
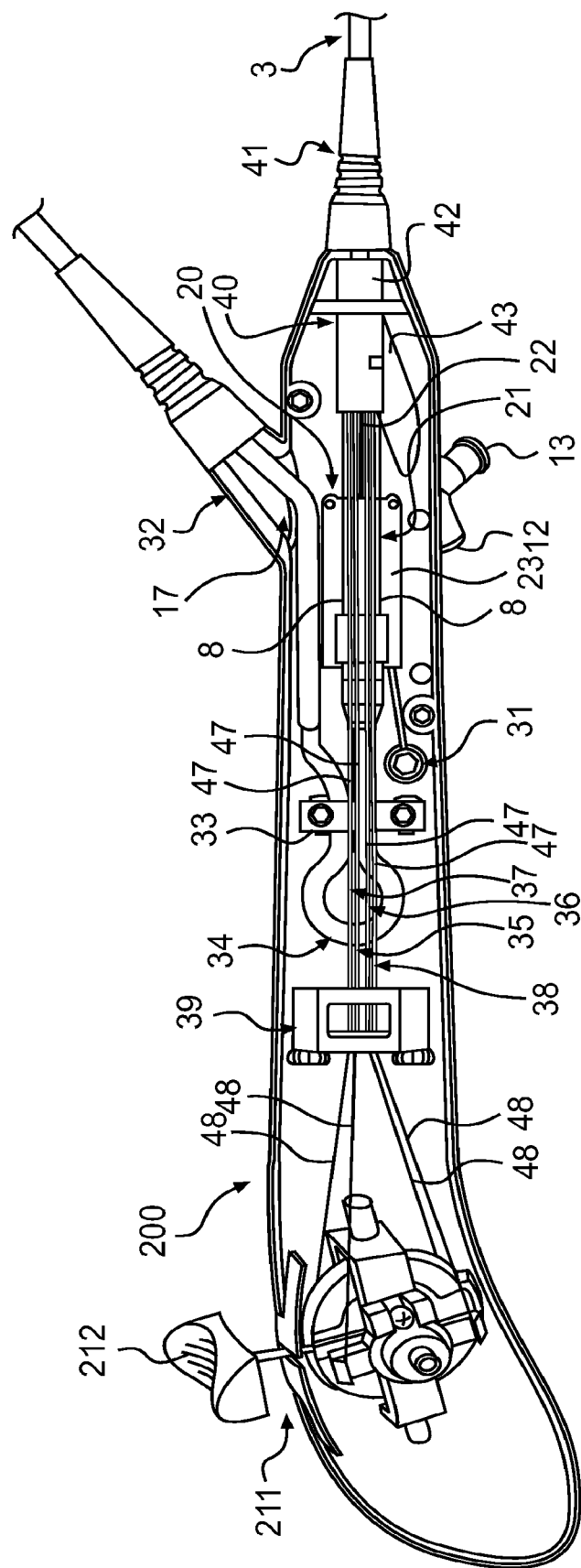
FIG. 7 illustrates a plan view of parts of a handle assembly of another medical device, according to an exemplary disclosed embodiment.

FIG. 7 illustrates another embodiment of a handle assembly 200 according to an exemplary disclosed embodiment. Handle assembly 200 may include substantially the same features as handle assembly 2 discussed above. A steering mechanism 211 of handle assembly 200, however, may include a single actuator 212 for steering elongate member 3 in the first and second planes. Actuator 212 may be embodied as a joystick that is substantially similar to the steering mechanism disclosed in U.S. Patent Application Publication No. 2010/0121147 to Oskin et al., which is incorporated herein by reference in its entirety.

Figure 8:
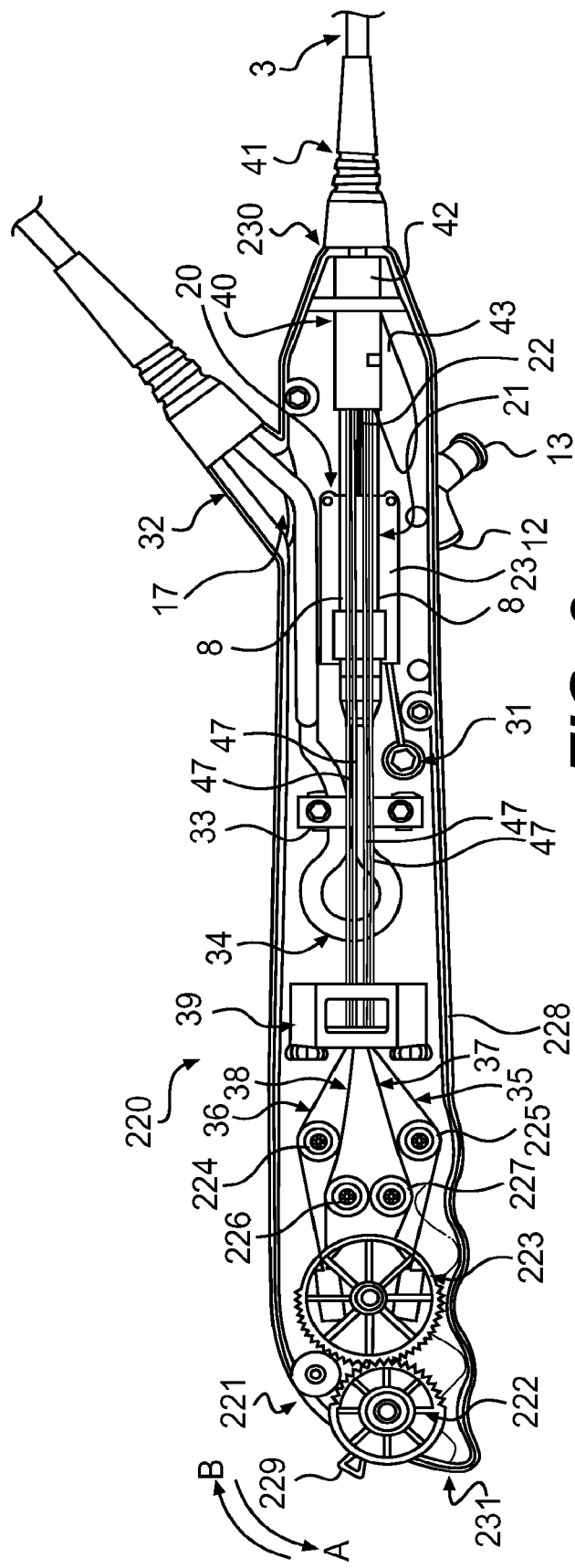
FIG. 8 illustrates a plan view of parts of a handle assembly of another medical device, according to an exemplary disclosed embodiment.

FIG. 8 illustrates another embodiment of a handle assembly 220 according to an exemplary disclosed embodiment. Handle assembly 220 may include substantially the same features as handle assembly 2 discussed above. In the embodiment of FIG. 8, a steering mechanism 221 may include a first gear 222, a second gear 223, a first pulley 224, a second pulley 225, a third pulley 226, and a fourth pulley 227. First and second control members 35, 36 may coupled to second gear 223 and may extend to distal portion 5 and be coupled to elongate member 3 at or near tip 9. Furthermore, first control member 35 may be partially wrapped around first pulley 224, and second control member 36 may be partially wrapped around second pulley 225. First and second pulleys 224, 225 may reduce the load on first and second control members 35, 36 when, for example, first and second control members 35, 36 are retracted to deflect distal portion 5 of elongate member 3.

First gear 222 and second gear 223 may be coupled together by their respective teeth. First gear 222 may partially extend external a handle housing 228 and include a lever 229 configured to actuate (i.e., rotate) first gear 222. Rotation of first gear 222 may then rotate second gear 223, thereby pulling proximally either first control member 35 or second control member 36 based on the direction of actuation of lever 229. For example, actuating lever 229 downwards, as indicated by direction arrow "A" of FIG. 8, may cause second gear 223 to rotate and pull on first control member 35. First control member 35 then may move distal portion 5 of elongate member 3 in the first direction along the first plane (e.g., down). Actuating lever 229 upwards, as indicated by direction arrow "B" of FIG. 8, may cause second gear 223 to rotate and pull on second control member 36. Second control member 36 then may move distal portion 5 of elongate member 3 in the second direction along the first plane (e.g., up).

Although not illustrated in FIG. 8, it should be appreciated that steering mechanism 221 may also include a third gear and a fourth gear having a similar arrangement and features as first and second gears 222, 223. Third and fourth control members 37, 38 may be coupled to the fourth gear and may extend distally to distal portion 5 and be coupled to elongate member 3 at or near tip 9. Third control member 37 may be partially wrapped around third pulley 226, and fourth control member 38 may be partially wrapped around fourth pulley 227. Third and fourth pulleys 226, 227 may reduce the load on third and fourth control members 37, 38 when, for example, third and fourth control members 37, 38 are retracted to deflect distal portion 5 of elongate member 3. Actuating a lever coupled to the third gear upwards and downwards may cause the fourth gear to rotate and pull on either third control member 37 or fourth control member 38 to deflect distal portion 5 of elongate member 3 in either the first or second direction along the second plane (e.g., left or right).

It should be appreciated that ureteroscope 1 may have an ergonomic structure for improved handling by a user. For example, handle assembly 200 of FIG. 7 may include a curved configuration for improved gripping by a user's hand. In addition, handle assembly 220 of FIG. 8 may include grooves for the respective fingers of a user's hand, thus improving the grip and comfort of ureteroscope 1.

FIGS. 9A-9D illustrate elongate member 3 according to an exemplary embodiment. Elongate member 3 may vary in stiffness between proximal portion 4, medial portion 6, and distal portion 5. For example, proximal portion 4 may be stiffer than medial portion 6, and medial portion 6 may be stiffer than distal portion 5. Such a configuration may minimize compression and twisting of elongate member 3 to allow elongate member 3 to be easily advanced through body cavities or lumens, while also providing deflection of distal portion 5. Elongate member 3 may also include a hub interface 51 disposed on proximal end 41 of elongate member 3. Hub interface 51 may connect elongate member 3 to handle assembly 2 and may provide torsion and tensile strength at the connection point between elongate member 3 and handle assembly 2. In one embodiment, hub interface 51 may be integrally formed with handle assembly 2 by, for example, injection molding. In other embodiments, hub interface 51 may be non-integrally formed with handle assembly 2 and may be connected thereto by, for example, adhesive bonding or mechanical connections, such as male and female threaded connections, quick lock connectors, snap connectors, and the like. In certain embodiments, distal portion 5 may include a length between 3 and 5 centimeters, medial portion 6 may include a length between 1 and 3 centimeters, and proximal portion 4 may include a length between 55 and 65 centimeters. It should be appreciated, however, that each of proximal portion 4, medial portion 6, and distal portion 5 may include any other suitable length.

Figure 9A:
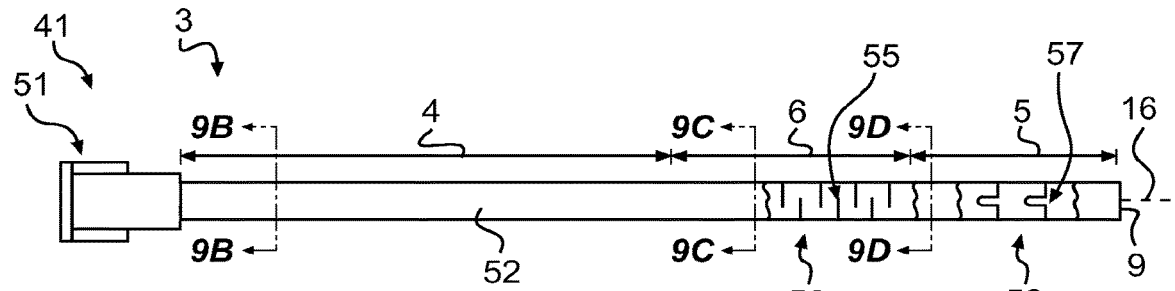
FIG. 9A illustrates a schematic view of an elongate member of a medical device, according to an exemplary disclosed embodiment.
Figure 9B:
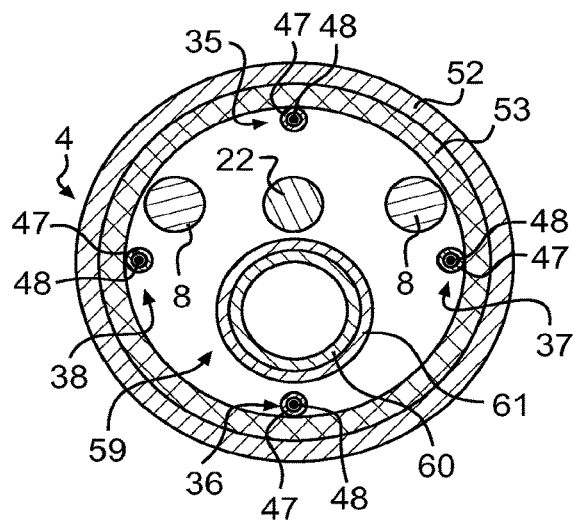
FIG. 9B illustrates a cross-sectional view of the elongate member of FIG. 9A, according to an exemplary disclosed embodiment.
Figure 9C:
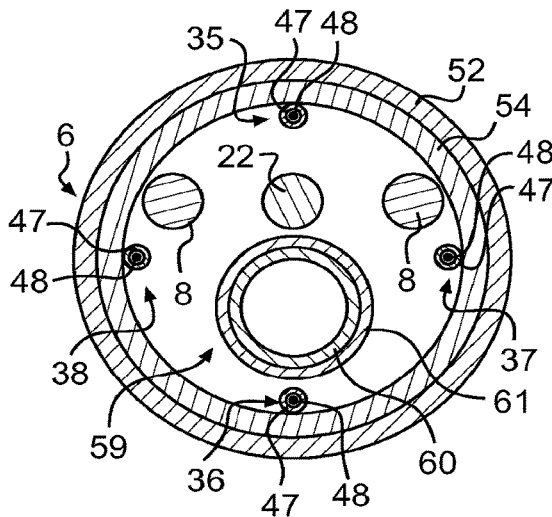
FIG. 9C illustrates another cross-sectional view of the elongate member of FIG. 9A, according to an exemplary disclosed embodiment.
Figure 9D:
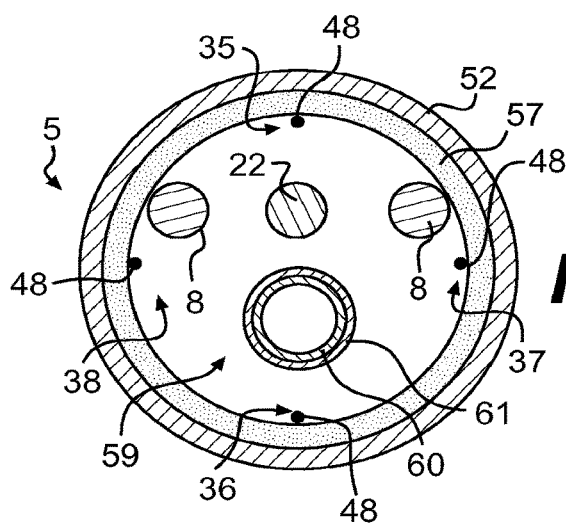
FIG. 9D illustrates another cross-sectional view of the elongate member of FIG. 9A, according to an exemplary disclosed embodiment.

FIGS. 9B-9D illustrate cross-sectional views of proximal portion 4, medial portion 6, and distal portion 5, respectively, according to an exemplary embodiment. Elongate member 3 may include an outer sleeve 52 encasing proximal portion 4, medial portion 6, and distal portion 5. Outer sleeve 52 may comprise of any number of polymer jackets including, as examples, polyethylene, such as polyethylene having a molecular weight in the range of 50,000 to 100,000; nylon, such as nylon 12, nylon 4-6, and nylon 6-6; Pebax (polyether block amides); polyurethane; polytetrafluoroethylene (PTFE); particularly fluorinated ethylene propylene (FEP) copolymers; and polyethylene impregnated with PTFE. Outer sleeve 52 may vary the stiffness of elongate member 3, if desired, or may provide improved torque transfer and/or other desirable structural properties. Additionally, outer sleeve 52 may be used as one convenient method for securing proximal portion 4, medial portion 6, and distal portion 5 together. In the embodiments of FIGS. 9A-9D, outer sleeve 52 may be formed of polyethylene.

In certain embodiments, outer sleeve 52 may include a hydrophilic coating or a silicone coating to ease the passage of elongate member 3 into the patient. Such a hydrophilic coating may be, as examples, N-vinyl pyrrolidone, polyvinyl alcohol, and polyvinyl pyrrolidone. The hydrophilic coating may be accomplished by coating outer sleeve 52 with a primer, such as Bayhydrol 110 (an anionic dispersion of an aliphatic polyester urethane resin in water/n-methyl-2pyrrolidone) and then bonding a primary layer over the primer. The primary layer may be, as examples, an acrylamide or a polyurethane-based acrylamide. Alliphatic polyether and polyester polyurethanes also may be used as lubricous coatings.

As shown in FIG. 9B, proximal portion 4 may include materials configured to provide pushability, stiffness, and kink resistance to elongate member 3. For example, proximal portion 4 may include a reinforcement sheath 53, encased by outer sleeve 52, that may extend from proximal end 41 of elongate member 3 to or immediately proximal medial portion 6. Reinforcement sheath 53 may include a coiled configuration of tightly wound flat wire or polymeric elements. The coiled configuration may provide column strength and torsional rigidity to elongate member 3 at proximal portion 4, which may allow elongate member 3 to be advanced through body lumens and/or cavities. The coiled configuration may also provide kink resistance to prevent proximal portion 4 from collapsing due to bending forces on proximal portion 4. In certain embodiments, reinforcement sheath 53 may include a wall thickness between 0.003" and 0.06", and may include a length between 65 cm and 70 cm.

As shown in FIGS. 9A and 9C, medial portion 6 may include materials configured to provide passive deflection of elongate member 3. For example, medial portion 6 may include a deflection sheath 54, encased by outer sleeve 52, and comprised of a similar coiled configuration of material as reinforcement sheath 53; however, the coiled material of medial portion 6 may include a suitable laser cut pattern 55. FIG. 9A shows a cut away portion 56 of outer sleeve 52 for the purposes of illustrating laser cut pattern 55. Laser cut pattern 55 may include slots cut 180° relative to each other and spaced an even distance apart from each other. The slots may be V-shaped, semi-circle, wave-shaped, or any other suitable shape. In certain embodiments, the slots may include a pitch of 0.008", and each slot may include a width between 0.001" and 0.0025". Accordingly, deflection sheath 54 may include a suitable flexibility to deflect and conform to the shape and anatomies of body lumens and/or cavities. In some embodiments, medial portion 6 may be configured to deflect up to 105° relative to longitudinal axis 16 of elongate member 3 in one or more directions from longitudinal axis 16.

As shown in FIGS. 9A and 9D, distal portion 5 may include materials configured to provide active deflection of elongate member 3. In other words, distal portion 5 may be configured to deflect in one or more directions (e.g., the first and second direction along the first plane and the first and second directions along the second plane, such as up, down, left, and right) upon actuation of control members 35, 36, 37, 38. Distal portion 5 may include, for example, a plurality of deflection segments 57 encased by outer sleeve 52. FIG. 9A shows a cut away portion 58 of outer sleeve 52 for the purposes of illustrating deflection segments 57. Deflection segments 57 may include, for example, a plurality of articulation joints substantially similar to any of the articulation joints disclosed in U.S. Patent Application Publication No. 2010/0076266 to Boulais et al. In certain embodiments, deflection segments 57 may be configured to deflect distal portion 5 up to 270° relative to longitudinal axis 16 of elongate member 3 along the first plane and along the second plane. In other embodiments, deflection segments 57 may be configured to deflect distal portion 5 up to 270° relative to longitudinal axis 16 of elongate member 3 in one of the first plane and the second plane, and up to 90° relative to longitudinal axis 16 of elongate member 3 in the other of the first plane and the second plane.

As shown in FIGS. 9B-9D, a working channel 59 may extend longitudinally through proximal portion 4, medial portion 6, and distal portion 5. Working channel 59 may be in communication with ports 12, 13 and may be defined by an inner sheath 60 and an outer sheath 61. Inner sheath 60 may be formed of any suitable material having a smooth surface configured to ease the passage of one or more instruments through working channel 59. For example, inner sheath 60 may be formed of PTFE or high density polyethylene. Outer sheath 61 may be comprised of any suitable material configured to provide kink resistance, yet still provide flexibility for working channel 59. For example, outer sheath 61 may include a braided configuration of tightly wound wires or polymeric elements. It should be appreciated that in certain embodiments, a polymeric jacket may be disposed over outer sheath 61, including, as examples, Pebax, polyimide, and fluorinated ethylene propylene. Furthermore, working channel 59 may taper from a larger diameter at proximal portion 4 to a smaller diameter at distal portion 5. The tapering diameter of working channel 59 towards distal portion 5 may help promote active deflection of distal portion 5. In addition, the tapering diameter of working channel 59 may promote an increased flow rate of a fluid delivered therethrough. For example, a suitable fluid, such as water, saline, or gas, introduced via port 13 and delivered through tapering working channel 59 may have a higher flow rate as it exits tip 9 relative to a working channel having a substantially constant diameter, since the smaller diameter of distal portion 5 may restrict the fluid traveling from the larger diameters of proximal portion 4 and medial portion 6.

FIGS. 9B-9D further illustrate that illumination units 8 of illumination system 21 and electrical wires 22 of camera system 20 may extend longitudinally through proximal portion 4, medial portion 6, and distal portion 5. It should be appreciated that illumination units 8 may be bundled together or may be separated, and electrical wires 22 may be bundled together or may be separated. In addition, control members 35, 36, 37, 38 may extend longitudinally through proximal portion 4, medial portion 6, and distal portion 5. Control members 35, 36, 37, 38 may be disposed 90° relative to each other radially around the lumen of elongate member 3. Outer jackets 47 may terminate at or proximal to distal portion 5. In other words, only control wires 48 of control members 35, 36, 37, 38 may extend along distal portion 5. The terminal ends of outer jackets 47 may be attached to medial portion 6 by any suitable fastener. Moreover, control wires 48 may be attached to an inner surface of distal portion 5, e.g., the inner surfaces of deflection segments 57, by any suitable fastener at or near tip 9. Alternatively, control wires 48 may be fastened within the walls of deflection segments 57. Accordingly, such a configuration of control members 35, 36, 37, 38 may facilitate the deflection of distal portion 5.

FIGS. 10A-10D illustrate another embodiment of an elongate member 300 according to an exemplary embodiment. Similar to elongate member 3, elongate member 300 may vary in stiffness between a proximal portion 304, a medial portion 306, and a distal portion 305. Elongate member 300 may also include working channel 59, illumination units 8, electrical wires 22, and control members 35, 36, 37, 38 in a similar arrangement as discussed above with regards to FIGS. 9A-9D. In addition, elongate member 300 may include hub interface 51.

Elongate member 300 may also include an outer sleeve 352 encasing proximal portion 304, medial portion 306, and distal portion 305. Outer sleeve 352 may comprise of any number of polymer jackets. In the embodiments of FIG. 10A-10D, outer sleeve 352 may include a first section 341 formed of a material having a first rigidity, and a second section 342 formed of a material having a second rigidity less than the first rigidity. For example, first section 341 may be formed of high durometer Pebax, and second section 342 may be formed of a low durometer Pebax. The high durometer Pebax of first section 341 may span proximal portion 304 to promote pushability, torque, and kink resistance to elongate member 300, and the low durometer Pebax of second section 342 may span medial portion 306 and distal portion 305 to facilitate deflection of elongate member 300. Furthermore, it should be appreciated that first and second sections 341, 342 may be integrally formed by, for example, extrusion, or may be separate sections attached together by a suitable fastening means, such as an adhesive or weld.

As shown in the cross-sectional views of elongate member 300 in FIGS. 10B and 10C, proximal portion 304 and medial portion 306 may include a first reinforcement sheath 353 surrounding a second reinforcement sheath 363 that may both extend from a proximal end 341 of elongate member 300 to or immediately proximal distal portion 305. First reinforcement sheath 353 may include a braided configuration of tightly wound wires or polymeric elements. Second reinforcement sheath 363 may include a coiled configuration of tightly wound flat wire or polymeric elements.

The combination of the high durometer Pebax of first section 341, first reinforcement sheath 353, and second reinforcement sheath 363 may provide pushability, column strength, and torsional rigidity to elongate member 300 at proximal portion 304, which may allow elongate member 300 to be advanced through body lumens and/or cavities. Moreover, such a combination may provide kink resistance to prevent proximal portion 304 from collapsing due to bending forces on proximal portion 304.

The combination of the low durometer Pebax of second section 342, first reinforcement sheath 353, and second reinforcement sheath 363 may provide passive deflection of elongate member 300 at medial portion 306. Accordingly, such a combination at medial portion 306 may provide a suitable flexibility for elongate member 300 to deflect and conform to the shape and anatomies of body lumens and/or cavities.

As shown in FIG. 10A and the cross-sectional view of elongate member 300 in FIG. 10D, distal portion 305 may include materials configured to provide active deflection of elongate member 300. In other words, distal portion 305 may be configured to deflect in one or more directions (e.g., the first and second direction along the first plane and the first and second directions along the second plane) upon actuation of control members 35, 36, 37, 38. Similar to distal portion 5 of elongate member 3, distal portion 305 of elongate member 300 may include, for example, deflection segments 57 encased by first reinforcement sheath 353 and outer sleeve 352. FIG. 10A shows a cut away portion 356 of outer sleeve 352 and first reinforcement sheath 353 for the purposes of illustrating deflection segments 57.

FIGS. 11A-11D illustrate another embodiment of an elongate member 400 according to an exemplary embodiment. Similar to elongate member 3, elongate member 400 may vary in stiffness between a proximal portion 404, a medial portion 406, and a distal portion 405. Elongate member 400 may also include working channel 59, illumination units 8, electrical wires 22, and control members 35, 36, 37, 38 in a similar arrangement as discussed above with regards to FIGS. 9A-9D. In addition, elongate member 400 may include hub interface 51.

Elongate member 400 may include outer sleeve 52 encasing proximal portion 404, medial portion 406, and distal portion 405. Outer sleeve 52 may comprise any number of polymer jackets. In the embodiments of FIGS. 11A-11D, outer sleeve 52 may be formed of polyethylene.

As shown in the FIG. 11A and the cross-sectional views of elongate member 400 in FIGS. 11B-11D, elongate member 400 may include a single tube 407 formed of, for example, stainless steel or polymeric materials, spanning proximal portion 404, medial portion 406, and distal portion 405. Along proximal portion 404, tube 407 may include a first laser cut section 408; along medial portion 406, tube 407 may include a second laser cut section 409; and along distal portion 405, tube may include a third laser cut section 410. First laser cut section 408 may include a laser cut pattern configured to promote pushability and torsional strength of elongate member 400. For example, first laser cut section 408 may include a relatively small number of laser cut slots spaced relatively far apart. In other words, first laser cut section 408 may include slots having a relatively large pitch, such as, for example, between 0.04" and 0.06". Second laser cut section 409 may include a laser cut pattern configured to promote flexibility for passive deflection and torsional strength of elongate member 400. For example, second laser cut section 409 may include a jigsaw pattern or a number of laser cut slots greater than the number of slots in first laser cut section 408 and having a smaller pitch relative to the slots of first laser cut section 408. Third laser cut section 410 may include a laser cut pattern configured to promote high flexibility for active deflection and low torsional strength for elongate member 400. For example, third laser cut section 410 may include a number of laser cut slots greater than the number of slots in both first laser cut section 408 and second laser cut section 409, and having a smaller pitch relative to the slots in both first laser cut section 408 and second laser cut section 409. FIG. 11A shows cut away portions 418, 419, 420 of outer sleeve 52 for the purposes of illustrating first, second, and third laser cut sections 408, 409, 410.

FIGS. 12A-12D illustrate another embodiment of an elongate member 500 according to an exemplary embodiment. Similar to elongate member 3, elongate member 500 may vary in stiffness between a proximal portion 504, a medial portion 506, and a distal portion 505. Elongate member 500 may also include working channel 59, illumination units 8, electrical wires 22, and control members 35, 36, 37, 38 in a similar arrangement as discussed above with regards to FIGS. 9A-9D. In addition, elongate member 500 may include hub interface 51.

Elongate member 500 may include outer sleeve 52 encasing proximal portion 504, medial portion 506, and distal portion 505. Outer sleeve 52 may comprise any number of polymer jackets. In the embodiments of FIGS. 12A-12D, outer sleeve 52 may be formed of polyethylene.

Figure 12A:
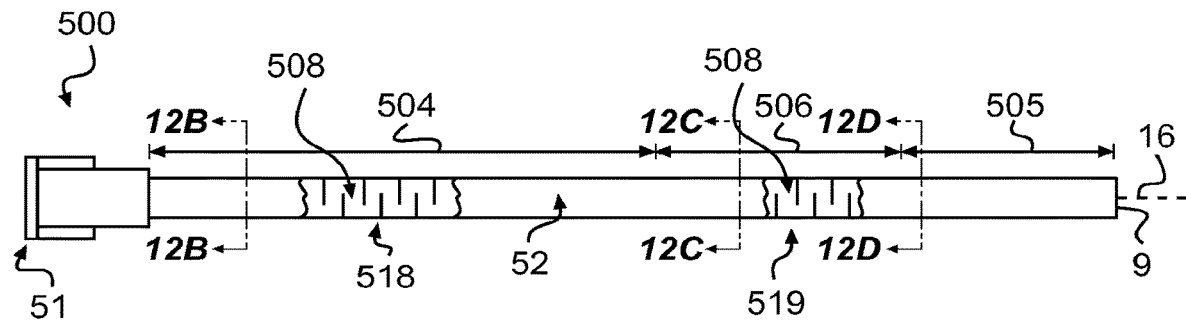
FIG. 12A illustrates a schematic view of another elongate member of a medical device, according to an exemplary disclosed embodiment.
Figure 12B:
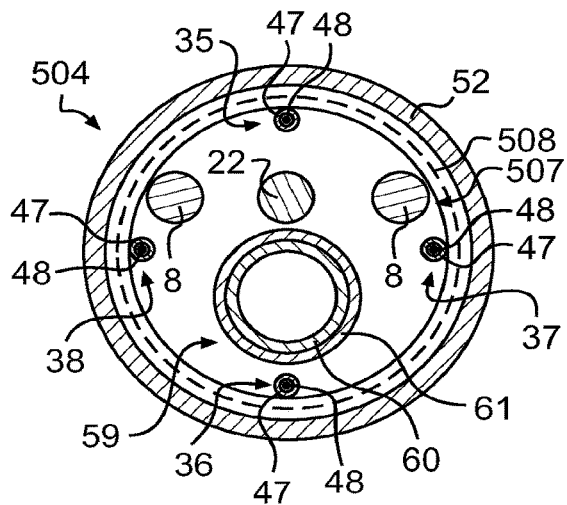
FIG. 12B illustrates a cross-sectional view of the elongate member of FIG. 12A, according to an exemplary disclosed embodiment.
Figure 12C:
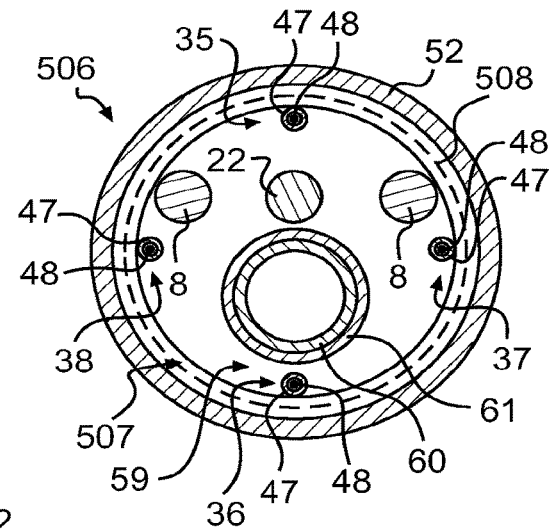
FIG. 12C illustrates another cross-sectional view of the elongate member of FIG. 12A, according to an exemplary disclosed embodiment.
Figure 12D:
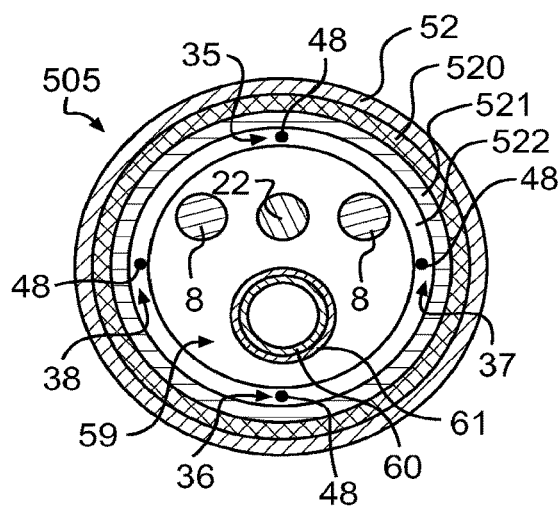
FIG. 12D illustrates another cross-sectional view of the elongate member of FIG. 12A, according to an exemplary disclosed embodiment.

As shown in the cross-sectional views of elongate member 500 in FIGS. 12B and 12C, proximal portion 504 and medial portion 506 may include materials configured to provide passive deflection of elongate member 500. For example, proximal portion 504 and medial portion 506 may include a single tube 507 formed of, for example, stainless steel or polymeric materials, having a suitable laser cut pattern 508. FIG. 12A shows cut away portions 518, 519 of outer sleeve 52 for the purposes of illustrating laser cut pattern 508. Laser cut pattern 508 may include slots cut 180° relative to each other and spaced an even distance apart from each other. The slots may be V-shaped, semi-circle, wave-shaped, or any other suitable shape. In certain embodiments, the slots may include a pitch of 0.008", each slot may include a width between 0.001" and 0.0025". Accordingly, proximal and medial portions 504, 506 may include a suitable flexibility to deflect and conform to the shape and anatomies of body lumens and/or cavities. In some embodiments, proximal portion 504 and medial portion 506 may be configured to deflect up to 105° relative to longitudinal axis 16 of elongate member 500 in one or more directions from longitudinal axis 16.

Distal portion 505 may be configured for active deflection of elongate member 500 by, for example, actuation of control members 35, 36, 37, 38. As shown in the cross-sectional view of elongate member 500 in FIG. 12D, distal portion 505 may include a first layer 520 formed of a polymeric material, such as Pebax, a second layer 521 formed of a loosely coiled stainless steel wires or polymeric materials, and a third layer 522 including a suitable polymeric material molded over control wires 48 of control members 35, 36, 37, 38. Actuation of control members 35, 36, 37, 38 may deflect distal portion 505 up to 270° relative to longitudinal axis 16 of elongate member 500 along the first plane and along the second plane. In other embodiments, distal portion 505 may be configured to deflect up to 270° relative to longitudinal axis 16 of elongate member 500 in one of the first plane and the second plane, and up to 90° relative to the longitudinal axis of elongate member 500 in the other of the first plane and the second plane.

Figure 13:
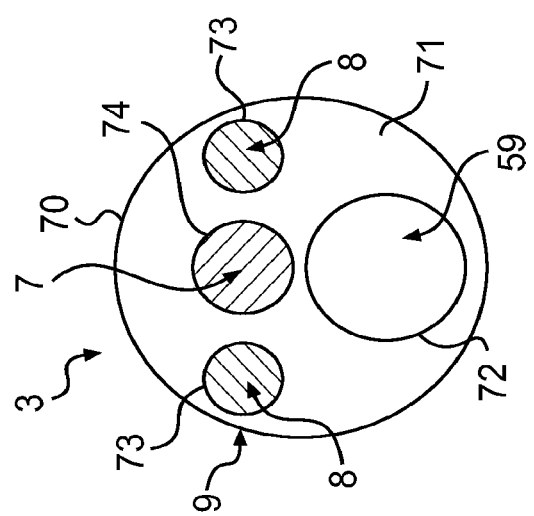
FIG. 13 illustrates a tip of a medical device, according to an exemplary disclosed embodiment.

FIG. 13 illustrates tip 9 of elongate member 3, 300, 400, 500 according to an exemplary embodiment, viewed from the distal end of elongate member 3, 300, 400, 500. Tip 9 may include a distal cap 70 having a number of openings on a distal face 71 of cap 70. The openings may include an opening 72 for working channel 59, openings 73 for illumination units 8, and an opening 74 for image sensor 7. As shown in FIG. 13, image sensor 7 may be disposed between illumination units 8, thus providing adequate illumination of a desired site for image capture. In addition, openings 73 for illumination units 8 and opening 74 for image sensor 7 may include windows or lenses to cover and protect illumination units 8 and image sensor 7 at distal face 71. Distal cap 70 may be integrally formed with elongate member 3, 300, 400, 500, or alternatively, may be a separate structure attached to tip 9 of elongate member 3, 300, 400, 500 by any suitable fastening means.

Figure 14:
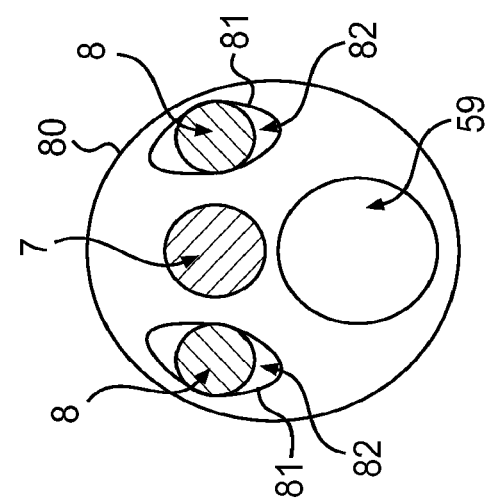
FIG. 14 illustrates a tip of a medical device, according to an exemplary disclosed embodiment.

FIG. 14 illustrates another embodiment of a distal cap 80 according to an exemplary embodiment. Distal cap 80 may be substantially similar to distal cap 70 of FIG. 11. In addition, openings 81 for illumination units 8 of distal cap 80 may include one or more diffusers 82. Diffusers 82 may be configured to spread the light discharged from illumination units 8 to produce a softer light and eliminate harsh light and hard shadows. Thus, the image captured by image sensor 7 may be softer and clearer. Diffusers 82 may include any suitable structure or materials for spreading the light from illumination units 8 including, as examples, ground glass, opal glass, grayed glass, and various white opaque plastics, such as titanium-filled acrylic and glass-filled polycarbonate. Diffusers 82 may also include a polycarbonate film having a rough and prism-like surface or a titanium dioxide adhesive applied over a distal face of distal cap 80 to cover illumination units 8 and bond illumination units 8 to distal cap 80. In some embodiments, distal cap 80 may be injection molded from any suitable, optically clear material that may be loaded with 1 to 15% titanium dioxide, and thus, the material of distal cap 80 may function as a diffuser.

Figure 15:
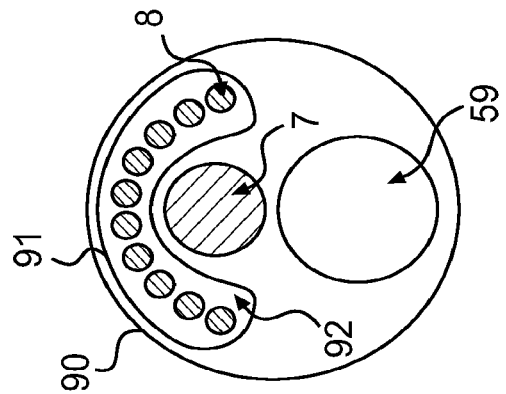
FIG. 15 illustrates a tip of a medical device, according to an exemplary disclosed embodiment.

FIG. 15 illustrates another embodiment of a distal cap 90 according to an exemplary embodiment. Distal cap 90 may be substantially similar to distal cap 70 of FIG. 13 and distal cap 80 of FIG. 14. In addition, distal cap 90 may be configured to accommodate illumination system 21 having a bundled arrangement of illumination units 8. The bundled arrangement may provide stronger illumination of a desired site for image capture. In addition, an opening 91 for illumination units 8 may include a diffuser 92, and the bundled arrangement of illumination units 8 and opening 91 may also be curved around image sensor 7.

Figure 16:
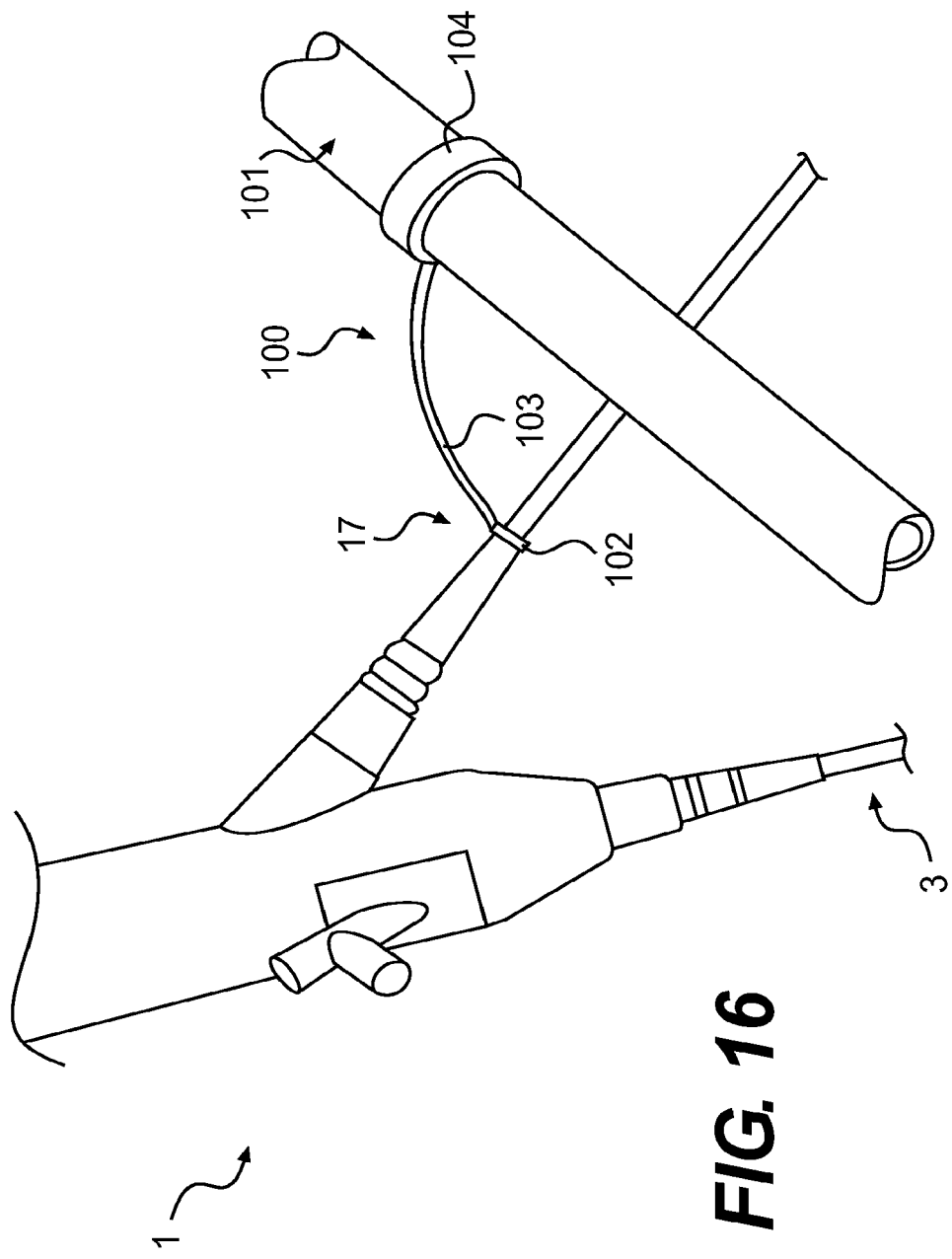
FIG. 16 illustrates a safety clip for a medical device, according to an exemplary disclosed embodiment.

FIG. 16 illustrates a safety clip 100 coupled to ureteroscope 1 according to an exemplary embodiment. Safety clip 100 may be configured to secure ureteroscope 1 to a structure 101, such as a bed rail, drape, cabinet, and the like, such that ureteroscope 1 may be prevented from falling on the floor and becoming contaminated in the event ureteroscope 1 slips from the user's hand. Safety clip 100 may include a first coupling member 102, a connecting member 103, and a second coupling member 104. First coupling member 102 and second coupling member 104 may include any suitable attachment means, such as a movable ring lock, a hook, and a lockable cuff. First coupling member 102 may be configured to attach to ureteroscope 1 at, for example, connector 17, elongate member 3, or a ring on handle assembly 2. Second coupling member 104 may be configured to attach to any suitable structure 101, such as a bed rail. Connecting member 103 may connect together first coupling member 102 and second coupling member 104. Connecting member 103 may be comprised of any suitable material configured to support the weight of ureteroscope 1, such as, for example, elastics, plastics, and polymeric materials.

Figure 17A:
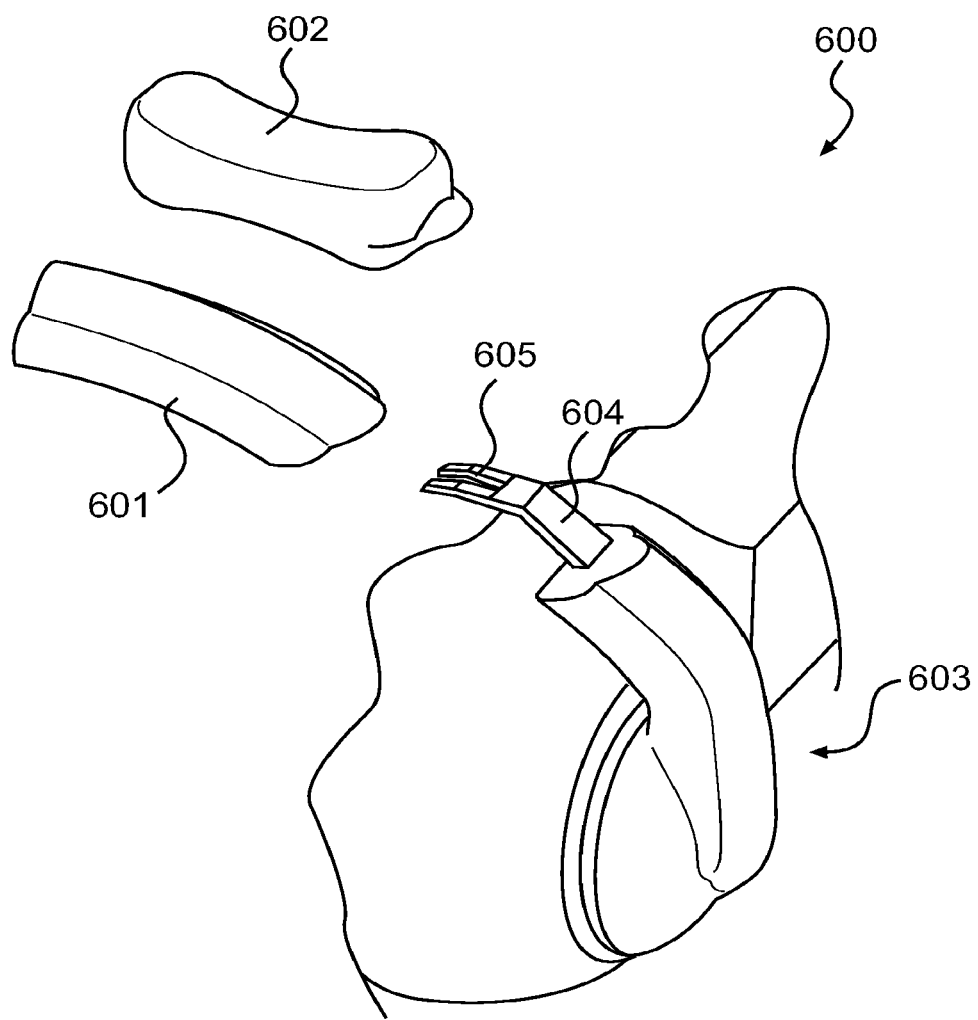
FIG. 17A illustrates a schematic view of an interchangeable lever system for a medical device, according to an exemplary disclosed embodiment.
Figure 17B:
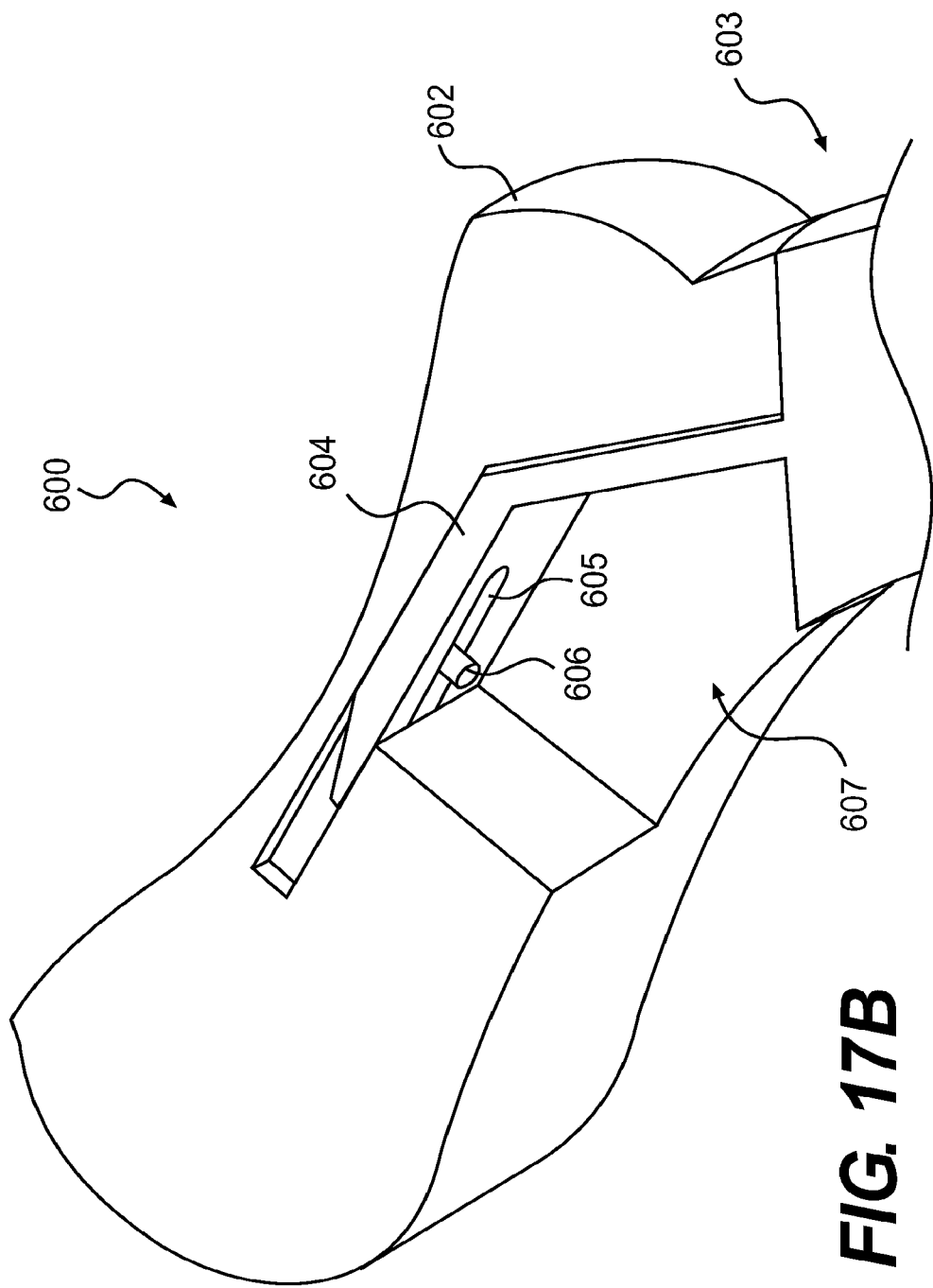
FIG. 17B illustrates a perspective view of the interchangeable lever system of FIG. 17A, according to an exemplary disclosed embodiment.

FIGS. 17A and 17B illustrate an interchangeable lever system 600 according to an exemplary embodiment. Interchangeable lever system 600 may be used with, for example, first actuator 14 and second actuator 15 of steering mechanism 11, and may be configured to readily interchange multiple different lever pads 601, 602 based on the preference of the user. For example, lever pad 601 may be softer and smoother relative to lever pad 602, and lever pad 602 may be more rigid, rough, and may ergonomically conform to the user's thumb. The user may switch between lever pads 601, 602 depending on, for example, comfort and performance.

FIG. 17A shows an actuator 603, such as first actuator 14 or second actuator 15 discussed above, with lever pads 601, 602 removed from actuator 603. Lever pads 601, 602 may be configured to attach to and detach from actuator 603. Actuator 603 may include a pad connection member 604 configured to receive either of lever pads 601, 602. More particularly, connection member 604 may include a slot 605 configured to connect to lever pads 601, 602 via a mechanical attachment, such as a snap fit.

FIG. 17B illustrates a perspective view of interchangeable lever system 600 according to an exemplary embodiment. As shown in FIG. 17B, lever pad 602 (shown with portions broken away) may be attached to actuator 603 via a snap fit between slot 605 of connection member 604 and a pin 606 of lever pad 602. More particularly, connection member 604 may be slid into a groove 607 of lever pad 602 until slot 605 slides and locks with pin 606. Lever pad 602 may be detached from actuator 603 by pulling lever pad 602 away from actuator 603 and releasing the snap fit. Other lever pads, such as lever pad 601, may then be coupled to actuator 603 by substantially the same configuration.

Any aspect set forth in any embodiment may be used with any other embodiment set forth herein. Every device and apparatus set forth herein may be used in any suitable medical procedure, may be advanced through any suitable body lumen and body cavity, and may be used for treatment of any suitable body portion. For example, the apparatuses and methods described herein may be used in any natural body lumen or tract, including those accessed orally, vaginally, or rectally.

The many features and advantages of the present disclosure are apparent from the detailed specification, and thus, it is intended by the appended claims to cover all such features and advantages of the present disclosure which fall within the true spirit and scope of the present disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

What is claimed is:

1. A medical device, comprising:
a member including at least a proximal portion including a proximal combination of layers of material, a medial portion including a medial combination of layers of material, and a distal portion extending to a distalmost end of the member and including a distal combination of layers of material, wherein the distal combination of layers includes an additional layer not included in the proximal combination of layers of material or the medial combination of layers of material;
a handle assembly connected to the proximal portion of the member, wherein the handle assembly includes an at least partially spherical portion at a proximal portion of the handle assembly; and
a steering mechanism, wherein the steering mechanism includes first and second actuators movable relative to the proximal portion of the handle assembly to deflect at least a portion of the distal portion of the member, wherein the first actuator is curved around a first portion of the at least partially spherical portion of the proximal portion of the handle assembly, and wherein the second actuator is curved around a second portion of the at least partially spherical portion of the proximal portion of the handle assembly,
wherein the first actuator is pivotable around the handle assembly in a first direction to deflect the at least a portion of the distal portion of the member in a first plane, and wherein the second actuator is pivotable around the handle assembly in a second direction to deflect the at least a portion of the distal portion of the member in a second plane different from the first plane.

2. The medical device of claim 1, wherein the first actuator and the second actuator are pivotable about different portions of the handle assembly.

3. The medical device of claim 1, wherein the steering mechanism includes a first cam, a second cam, and a plurality of control members housed within the handle assembly, wherein each control member of the plurality of control members is operably coupled to one of the first or second cams and extends through the member, and wherein the plurality of control members is coupled to the distal portion of the member.

4. The medical device of claim 3, wherein the first actuator is operably coupled to the first cam and the second actuator is operably coupled to the second cam, wherein actuation of the first actuator steers the distal portion of the member along the first plane, and wherein actuation of the second actuator steers the distal portion of the member along the second plane.

5. The medical device of claim 1, further comprising a lock mechanism, wherein the lock mechanism includes a tension knob configured to actuate between a locked position and an unlocked position.

6. The medical device of claim 1, wherein at least one of the first actuator or the second actuator includes a lever pad coupled to the remainder of the first actuator or the second actuator via a connection member.

7. The medical device of claim 6, wherein the connection member includes a slot, wherein the lever pad includes a pin, and wherein the lever pad is coupled to the connection member via a snap fit connection between the slot and the pin.

8. The medical device of claim 1, further comprising:
a camera system configured to capture images from a distal end of the member; and
an illumination system configured to provide illumination from the distal end of the member.

9. The medical device of claim 8, wherein the handle assembly includes a connector hub, wherein the connector hub is positioned on a distal portion of the handle assembly and is angled toward the member, and
wherein the medical device further comprises a connector configured to connect the handle assembly to a control module including one or more processing units for operating the camera system or the illumination system, wherein the connector is configured to be removably connected to the handle assembly via the connector hub.

10. A medical device, comprising:
a member including at least a proximal portion including a proximal combination of layers of material, a medial portion including a medial combination of layers of material, and a distal portion extending to a distalmost end of the member and including a distal combination of layers of material, wherein the distal portion includes at least one additional layer not included in the proximal combination of layers or the medial combination of layers;
a handle assembly connected to the proximal portion of the member, wherein the handle assembly includes an at least partially spherical portion at a proximal portion of the handle assembly; and
a steering mechanism, wherein the steering mechanism includes two actuators movable relative to the proximal portion of the handle assembly to deflect at least a portion of the distal portion of the member, the two actuators including a first actuator pivotable around the handle assembly in a first direction to deflect the at least a portion of the distal portion of the member in a first plane, and a second actuator pivotable around the handle assembly in a second direction to deflect the at least a portion of the distal portion of the member in a second plane different from the first plane.

11. The medical device of claim 10, wherein the actuators are curved around the at least partially spherical portion of the proximal portion of the handle assembly.

12. The medical device of claim 10, wherein the steering mechanism includes a first cam, a second cam, and a plurality of control members housed within the handle assembly, wherein each control member of the plurality of control members is operably coupled to one of the first or second cam and extends through the member, wherein the plurality of control members is coupled to the distal portion of the member, and wherein the distal portion of the member includes a plurality of deflection segments encased by an outer sleeve.

13. The medical device of claim 10, further comprising a lock mechanism, wherein the lock mechanism includes a tension knob configured to actuate between a locked position and an unlocked position.

14. A medical device, comprising:
a member including at least a proximal portion including a proximal combination of layers of material, a medial portion including a proximal combination of lavers of material, and a distal portion extending to a distalmost end of the member and including a distal combination of layers of material, wherein the distal combination of layers includes an additional layer not included in the proximal combination of layers or the medial combination of layers;
a handle assembly connected to the proximal portion of the member, wherein the handle assembly includes:
an at least partially spherical portion at a proximal portion of the handle assembly; and
a connector hub, wherein the connector hub is positioned on a distal portion of the handle assembly and is angled toward the member, and
a connector configured to connect the handle assembly to a control module including one or more processing units for operating a camera system or an illumination system, wherein the connector is configured to be removably connected to the handle assembly via the connector hub; and
a steering mechanism, wherein the steering mechanism includes two actuators movable relative to the proximal portion of the handle assembly to deflect at least a portion of the distal portion of the member, wherein the two actuators are curved around different portions of the at least partially spherical portion of the proximal portion of the handle assembly.

* * * * *